US012612373B2

(12) United States Patent

Verge et al.

(10) Patent No.: US 12,612,373 B2

(45) Date of Patent: Apr. 28, 2026

(54) BENZOXAZINE DERIVATIVES VITRIMERS

(71) Applicant: LUXEMBOURG INSTITUTE OF SCIENCE AND TECHNOLOGY (LIST), Esch-sur-Alzette (LU)

(72) Inventors: Pierre Verge, Esch-sur-Alzette (LU); Laura Puchot, Esch-sur-Alzette (LU); Acerina Trejo Machin, Esch-sur-Alzette (LU)

(73) Assignee: LUXEMBOURG INSTITUTE OF SCIENCE AND TECHNOLOGY (LIST), Esch-sur-Alzette (LU)

( * ) Notice: Subject to any disclaimer, the term of this patent is extended or adjusted under 35 U.S.C. 154(b) by 702 days.

(21) Appl. No.: 17/911,100

(22) PCT Filed: Mar. 4, 2021

(86) PCT No.: PCT/EP2021/055486

§ 371 (c)(1),
(2) Date: Sep. 12, 2022

(87) PCT Pub. No.: WO2021/180562

PCT Pub. Date: Sep. 16, 2021

(65) Prior Publication Data

US 2023/0147484 A1 May 11, 2023

(30) Foreign Application Priority Data

Mar. 12, 2020 (LU) ........................................ 101674

(51) Int. Cl.
*C07D 265/16* (2006.01)
*C08G 73/02* (2006.01)

(52) U.S. Cl.
CPC ....... *C07D 265/16* (2013.01); *C08G 73/0233* (2013.01)

(58) Field of Classification Search
CPC ..................................................... C07D 265/16
See application file for complete search history.

(56) References Cited

PUBLICATIONS

International Search Report for PCT/EP2021/055486 mailed Apr. 26, 2021.

Written Opinion for PCT/EP2021/055486 mailed Apr. 26, 2021.

M. Alvarez et al: "Structure-activity relationships among di- and tetramine disulfides related to benextramine", Journal of Medicinal Chemistry, vol. 30, No. 7, 1987, pp. 1186-1193, XP055692289, ISSN: 0022-2623, DOI: 10.1021/jm00390a011 scheme I; table I; p. 1192, right-hand column, paragraph 2; compound 27 abstract.

Wim Denissen et al: "Vitrimers: permanent organic networks with glass-like fluidity", Chemical Science, vol. 7, No. 1, 2016, pp. 30-38, XP055609548, ISSN: 2041-6520, DOI: 10.1039/C5SCO2223A cited in the application the whole document p. 36, section Disulfide exchange chemistry, figure 9.

Baris Kiskan: "Adapting benzoxazine chemistry for unconventional applications", Reactive and Functional Polymers, vol. 129, 2018, pp. 76-88, XP085405761, ISSN: 1381-5148, DOI: 10.1016/J.REACTFUNCTPOLYM.2017.06.009 cited in the application the whole document pp. 82-84, section 2.4. Benzoxazine-sulfur chemistry . . . , scheme 12.

*Primary Examiner* — Golam M Shameem

(74) *Attorney, Agent, or Firm* — Sandberg Phoenix & von Gontard, P.C.

(57) ABSTRACT

Disulfide-containing benzoxazine monomers of formula I

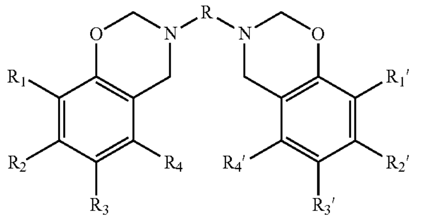

Also a process for synthesizing a disulfide-containing benzoxazine monomer of formula I comprises the following steps consisting of providing a mixture comprising an amino disulfide compound:$H_2N$—R—$NH_2$, wherein R is as defined for the monomer of formula I, an aldehyde derivative; phenolic derivatives, stirring the mixture under a temperature of from 50° C. to 130° C. for 1 h to 48 h, for obtaining the monomer of formula I; wherein the respective stoichiometry of the amino disulfide compound:aldehyde derivative:phenolic derivatives is $1:4:x_1+x_2$, with $x_1+x_2=2$ and $0<x_1;x_2<2$. Also a process for preparing a polybenzoxazine derivative vitrimer comprising a polymerization of the benzoxazine monomer at temperatures within the range of from 100° C. to 250° C. for 1 h to 24 h, for obtaining the polybenzoxazine derivatives vitrimer. Also polybenzoxazine derivative vitrimers, presenting at least one of the following characteristics of Tg values of from 0° C. to 250° C.; and relaxation temperature values, above the Tg values, of from 0° C. to 250° C.

9 Claims, 15 Drawing Sheets

4apds CAR PFA CAR-4apds $n' = 8\text{-}100$

BENZOXAZINE DERIVATIVES VITRIMERS

CROSS-REFERENCE TO RELATED APPLICATIONS

The present invention is the US national stage under 35 U.S.C. § 371 of International Application No. PCT/EP2021/055486 which was filed on Mar. 4, 2021, and which claims the priority of application LU101674 filed on Mar. 12, 2020 the contents of which (text, drawings and claims) are incorporated here by reference in its entirety.

FIELD

The invention is directed to the field of benzoxazine derivatives vitrimers and to a process of manufacturing thereof and the use of the vitrimers in various applications.

BACKGROUND

Composites are in almost all the cases produced from thermoset resins, a material of choice for numerous applications because of their dimensional stability, mechanical properties and creep/chemical resistance. However, as a result of their permanent molecular architecture, they are impossible to recycle or to reprocess, and ends up in landfills.

A chemical way to tackle this drawback is offered by the introduction of exchangeable chemical bonds, leading to dynamic cross-links. Polymer networks containing such exchangeable bonds are also known as covalent adaptable networks (CANs) (W. Denissen et al. —Wim Denissen, Johan M. Winne and Filip E. Du Prez, Chem. Sci., 2016, 7, 30-38). CANs may be further classified into two groups depending on their exchange mechanism, either dissociative or associative. In the first, chemical bonds are first broken and then formed again at another place. Diels Alder reactions are the most common mechanism of dissociative CANs. In the second, polymer networks do not depolymerise upon heating, but are characterized by a fixed cross-link density. Covalent bonds are only broken when new ones are formed, making these networks permanent as well as dynamic. The first reported associative CANs (2005) were based on photo-mediated reactions by using allyl sulfides for instance. Later, a similar exchange mechanism was introduced by using alternative radical generators with trithiocarbonates.

In 2011, Leibler et al. (D. Montarnal, M. Capelot, F. Tournilhac and L. Leibler, *Science,* 2011, 334, 965-968) extended the field of associative CANs by adding a suitable transesterification catalyst to epoxy/acid or epoxy/anhydride polyester-based networks, resulting in permanent polyester/polyol networks that show a gradual viscosity decrease upon heating. Such a distinctive feature of vitreous silica had never been observed in organic polymer materials. Hence, the authors introduced the name vitrimers for those materials.

Based on the pioneering work of Leibler et al. (previously mentioned), this new class of materials can be defined by some criteria. First, vitrimers are made of covalently bound chains forming an organic network, insoluble in solvents. This network is furthermore able to change its topology via associative exchange reactions and thermally triggered, resulting in the thermal malleability of the network. At higher temperatures, the viscosity of vitrimers is essentially controlled by chemical exchange reactions, giving a thermal viscosity decrease that follows the Arrhenius law.

Various vitrimer materials were developed based on the nature of dynamic associative exchange reactions, in particular sulfur-sulfur linkages. Recently, Pepels et al. (M. Pepels, I. Filot, B. Klumperman and H. Goossens, *Polym. Chem.,* 2013, 4, 4955-4965) reported dynamic networks based on thiol-disulfide exchange reactions, showing properties reminiscent of vitrimers.

In 2014, Martin et al. (R. Martin, A. Rekondo, A. Ruiz de Luzuriaga, G. Cabañero, H. J. Grande and I. Odriozola, *J. Mater. Chem. A,* 2014, 2, 5710-5715) demonstrated reprocessable elastomers using aromatic disulfide metathesis in poly(urea-urethane) networks. These networks showed quantitative self-healing at room temperature due to both dynamic hydrogen bonds formation and network reshuffling. In addition, Rekondo et al. (A. Rekondo, R. Martin, A. R. d. Luzuriaga, G. Cabañero, H. J. Grande and I. Odriozola, *Mater. Horiz.,* 2016, 3, 241-247) developed a fiber-reinforced polymer composite made of an epoxy resin and dynamic disulfide bonds, able to be reprocessed and recycled. 3D printed thermosets, although desirable, are inherently non-recyclable due to their permanently cross-linked networks, and Qi et al. developed a first example of recyclable 3D printable epoxy vitrimer (Qian Shi, Kai Yu, Xiao Kuang, Xiaoming Mu, Conner K. Dunn, Martin L. Dunn, Tiejun Wang and H. Jerry Qi, Mater Horiz., 2017, 4, 598-607).

Polybenzoxazines are a new type of thermoset with outstanding mechanical and thermal properties, as well as a strong irreversible adhesion to metallic substrates. As many other thermosets, they cannot be reshaped, re-processed, recycled or disassembled from metals parts. A few examples have been reported showing a reasonable level of healability (L. Zhang, Z. Zhao, Z. Dai, L. Xu, F. Fu, T. Endo, X. Liu, ACS Macro. Lett. 2019, 8, 5, 506-511 and Arslan M., Kiskan B., Y. Yagci, Sci. Rep. 2017, 7, 5207). However, polybenzoxazine remains a class of high performance materials without any demonstration of vitrimers capabilities neither reversible adhesion on metallic substrates.

SUMMARY

The invention has for technical problem to provide a solution to at least one drawback of the above cited prior art. For this purpose, the invention is directed to a disulfide-containing benzoxazine monomer of formula (I)

(I)

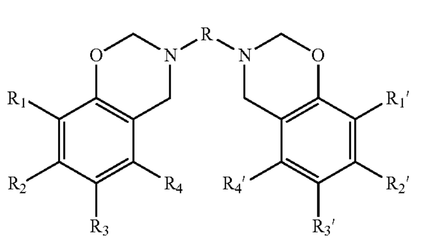

wherein R is:

(II)

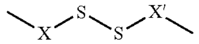

wherein, in formula (II), X and X' are, independently, a substituted or unsubstituted aliphatic $C_1$-$C_{20}$ alkyl group optionally containing heteroatoms; and/or a substituted or unsubstituted aliphatic $C_2$-$C_{20}$ alkenyl group optionally containing heteroatoms; and/or at least one substituted or unsubstituted $C_6$-$C_{20}$ aryl group; and/or at least one substituted or unsubstituted $C_6$-$C_{20}$ heteroaryl group; and/or at least one substituted or unsubstituted $C_6$-$C_{20}$ heterocyclic group, and/or at least one substituted or unsubstituted $C_3$-$C_8$ cycloalkyl group, the heteroatoms being selected from the groups consisting of N, O and S, and wherein a combination of $R_1$, $R_2$, $R_3$, $R_4$, substituents is selected from the group of the combinations consisting of $R_1$=$R_2$=$R_3$=$R_4$=H, $R_1$=$OCH_3$, $R_2$=$R_3$=$R_4$=H, $R_1$=$OCH_3$, $R_2$=$R_4$=$R_3$=alkyl group of $C_1$-$C_{15}$, $R_1$=$OCH_3$, $R_2$=$R_4$=H, $R_3$=CHO, $R_1$=$OCH_3$, $R_2$=$R_4$=H, $R_3$=$(CH_2)_{n:1\text{-}15}$COOH, $R_1$=$OCH_3$, $R_2$=$R_4$=H, $R_3$=$(CH_2)_{n:1\text{-}15}$CH=$CH_2$, $R_1$=$OCH_3$, $R_2$=$R_4$=H, $R_3$=CH=$CHCH_3$, $R_1$=$R_2$=$R_4$=H, $R_3$=$(CH_2)_{n:1\text{-}15}$COOH, $R_1$=$R_2$=$R_4$=H, $R_3$=CH=CHCOOH, $R_1$=$OCH_3$, $R_2$=$R_4$=H, $R_3$=CH=CHCOOH, at least one of $R_1$, $R_2$, $R_3$, $R_4$ is an aliphatic alkyl group of $C_1$-$C_{15}$, the rest being H, $R_1$=$R_3$=$R_4$=H, and $R_2$ = 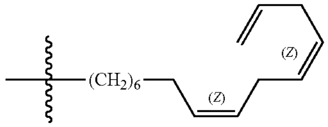 ,

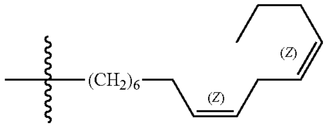 ,

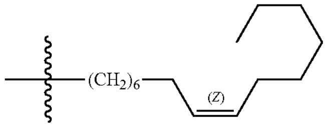 and/or

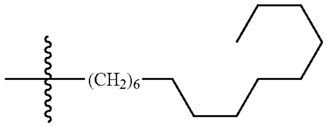 ;

$R_3$=$R_4$=H, $R_1$=COOH $R_2$ = 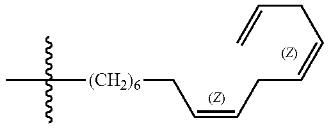 ,

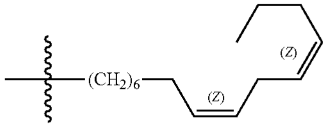 ,

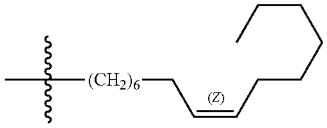 and/or

-continued

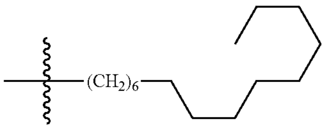 ;

$R_1$=H, $R_2$=OH, $R_3$=H, and $R_4$ = 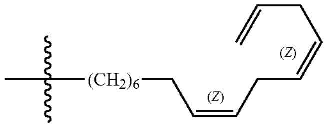 ,

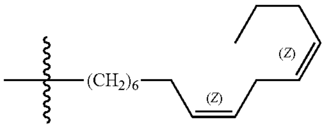 ,

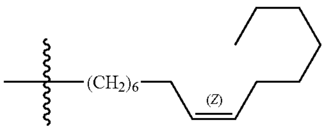 and/or

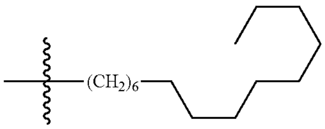 ;

$R_1$=H, $R_3$=OH, $R_4$=H and $R_2$ = 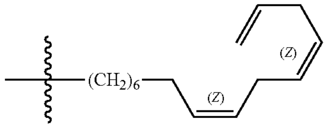 ,

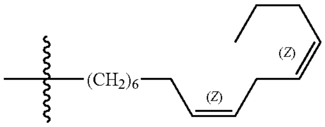 ,

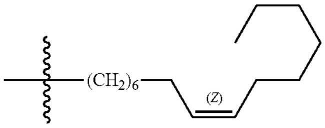 and/or

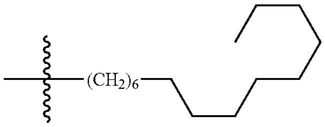 ;

$R_1$=$CH_3$, $R_2$=OH, $R_3$=H, $R_4$ = 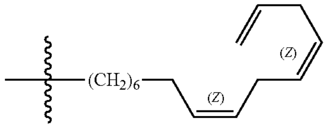 ,

-continued

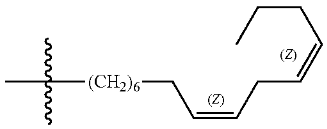
,

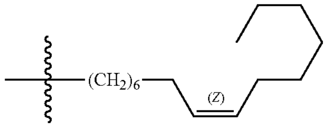
and/or

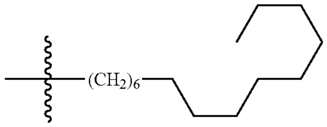
;

$R_3=R_4=H$, $R_1=OH$ and $R_2$ = 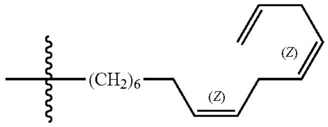
,

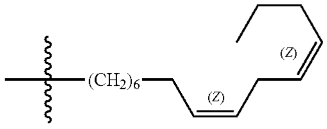
,

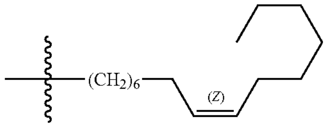
and/or

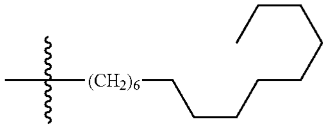
;

$R_2=R_3=R_4=H$ and $R_1=(CH_2)_{n:1\text{-}15}CH=CH_2$,
$=R_3=R_4=H$ and $R_2=(CH_2)_{n:1\text{-}15}CH=CH_2$,
$R_1=R_2=R_4=H$ and $R_3=(CH_2)_{n:1\text{-}15}CH=CH_2$,
$R_1=R_3=R_4=H$ and $R_2=$

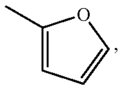
, and
$R_1=R_2=R_4=H$ and $R_3=$

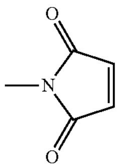
;

or mixture thereof wherein a combination of $R_1'$, $R_2'$, $R_3'$, $R_4'$ substituents is as defined for the combination of $R_1$, $R_2$, $R_3$, $R_4$ substituents and is independent thereof.

In various embodiments, the compound: N,N'-(disulfanediylbis(methylene))bis(6-(2H-benzo[e][1,3] oxazin-3 (4H)-yl)hexan-1-amine is excluded. The disulfide-containing benzoxazine monomer of the invention is advantageously suited for obtaining polybenzoxazine derivatives vitrimers by a polymerization involving the benzoxazine ring opening and a self-polymerisation under heat, resulting to the polybenzoxazine derivatives vitrimers. Owing to the specific monomer starting product, the vitrimers of the invention present self-healing, reshaping, reprocessability and recycling properties. For the rest of the document, benzoxazine vitrimers will always refer to the polymerized form of the benzoxazine monomers.

The polybenzoxazine derivatives vitrimers properties are tightly connected to the properties of the benzoxazine monomer.

As may be seen from formula (I), the monomer includes a benzoxazine ring moiety, that allows the cross-linking of the monomer upon heating and that promotes the reprocessing thanks to reversible H-bonds it forms once cross-linked (vitrimers). The optional presence of alkyl groups on the benzoxazine ring moiety may enhance the processability of the monomer, which also results in the reprocessability of the benzoxazine derivatives vitrimers. The presence of a moiety consisting in diamine containing a disulfide bond is essential to form a dynamic and reversible network of the benzoxazine derivatives vitrimers, allowing the material to be recycled, reshaped and reprocessed. Accordingly, the essential features of the monomer of the invention rely on the benzoxazine-containing moiety and on disulfide bonds. The Tg of such polybenzoxazine may be of from −50° C. to 300° C.

Advantageously, in formula (II), X and X' may be, independently, a substituted or unsubstituted aliphatic $C_1$-$C_{15}$ alkyl group, better $C_1$-$C_8$ alkyl group, optionally containing heteroatoms N, O, S; and/or a substituted or unsubstituted aliphatic $C_2$-$C_{15}$ alkenyl group, better $C_2$-$C_8$ alkenyl group, optionally containing heteroatoms N, S, O; and/or at least one substituted or unsubstituted $C_6$-$C_{15}$ aryl group; and/or at least one substituted or unsubstituted $C_6$-$C_{15}$ heteroaryl group; and/or at least one substituted or unsubstituted $C_6$-$C_{15}$ heterocyclic group, and/or at least one $C_3$-$C_6$ cycloalkyl group.

In various embodiments, R may be selected from the group of moieties consisting of (A)

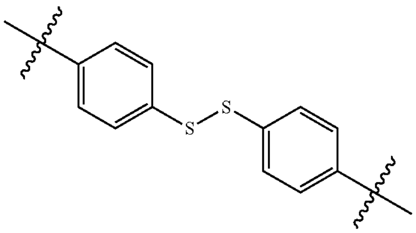

and

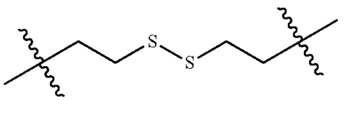
, and, independently, the combination of $R_1$, $R_2$, $R_3$, $R_4$, substituents and $R_1'$, $R_2'$, $R_3'$, $R_4'$, substituents being as defined for the combination of $R_1$, $R_2$, $R_3$, $R_4$, substituents and being independent thereof, may be selected from the group of the combinations consisting of:

$R_1$=$OCH_3$, $R_2$=$R_4$=$R_5$=H, $R_3$=alkyl group of $C_1$-$C_{15}$, $R_1$=$OCH_3$, $R_2$=$R_4$=H, $R_3$=$(CH_2)_{n:1-15}COOH$, $R_1$=$OCH_3$, $R_2$=$R_4$=H, $R_3$=$(CH_2)_{n:1-15}CH$=$CH_2$, $R_1$=$R_2$=$R_4$=H, $R_3$=$(CH_2)_{n:1-15}COOH$, at least one of $R_1$, $R_2$, $R_3$, and $R_4$ is an aliphatic alkyl group of $C_1$-$C_{15}$, the rest being H, $R_1$=$R_3$=$R_4$=H, and $R_2$ =

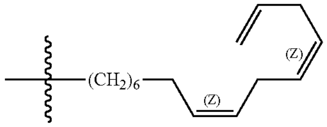

,

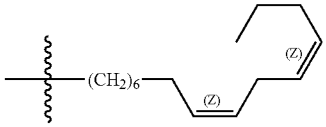

,

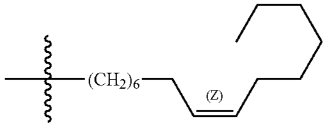

and/or

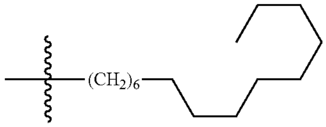

;

$R_3$=$R_4$=H, $R_1$=COOH $R_2$ =

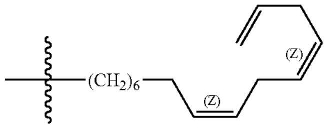

,

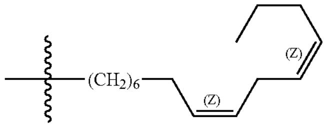

,

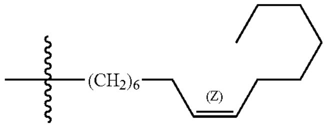

and/or

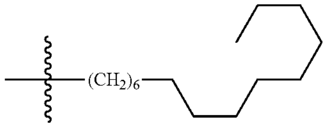

;

$R_1$=H, $R_2$=OH, $R_3$=H, and $R_4$ =

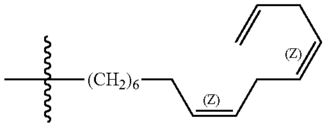

,

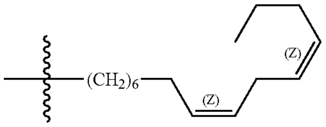

,

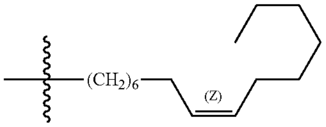

and/or

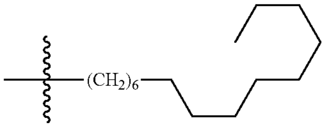

;

$R_1$=H, $R_3$=OH, $R_4$=H and $R_2$ =

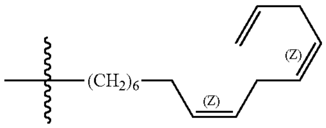

,

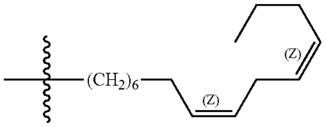

,

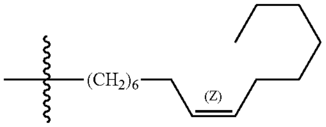

and/or

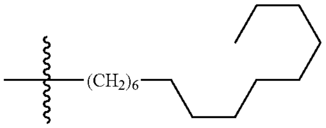

;

$R_1$=$CH_3$, $R_2$=OH, $R_3$=H, $R_4$ =

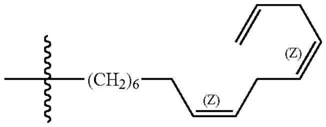

,

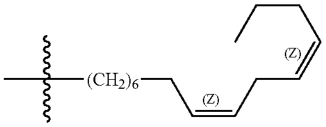

,

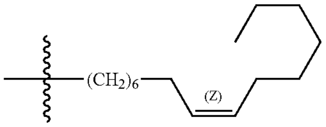

and/or

-continued

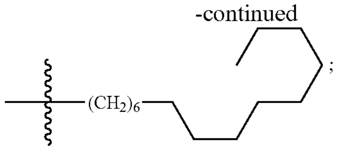

$R_3$=$R_4$=H, $R_1$=OH and $R_2$=

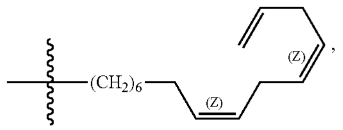

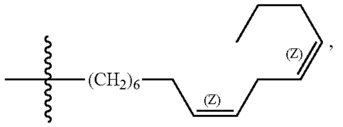

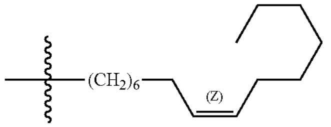

and/or

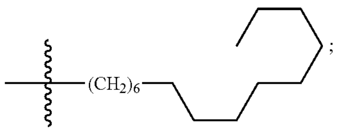

$R_2$=$R_3$=$R_4$=H and $R_1$=$(CH_2)_{n:1\text{-}15}CH{=}CH_2$,
$R_1$=$R_3$=$R_4$=H and $R_2$=$(CH_2)_{n:1\text{-}15}CH{=}CH_2$,
$R_1$=$R_2$=$R_4$=H and $R_3$=$(CH_2)_{n:1\text{-}15}CH{=}CH_2$,
$R_1$=$R_3$=$R_4$=H and $R_2$=

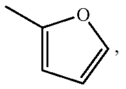

and
$R_1$=$R_2$=$R_4$=H and $R_3$=

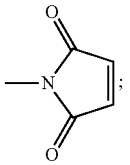

or mixtures thereof.

These compounds are in various instances due to the presence of long-chain alkyl groups, optionally including unsaturated bonds, such as C=C, methylene chains and/or substituents bearing cyclic hydrocarbons containing N or O in the ring on the benzoxazine ring moiety, promoting the processability of the monomer, which also results in the increased reprocessability of the benzoxazine derivatives vitrimers in terms of lower reprocessing temperature. The melt viscosities of such monomers are reduced compared to non-substituted ones or slightly substituted compounds such as bearing CH=CHCOOH, $-OCH_3$, —COOH groups. The vitrimers obtained using such monomers may exhibit lower Tg and reprocessing temperature compared to non-substituted ones or slightly substituted compounds, for example exhibiting a Tg range values of from −50° C. to 250° C., in various instances of from 0° C. to 200° C., for example of from 20° C. to 100° C., the reprocessing temperatures being higher than the Tg range values.

Most advantageous embodiments may be the compounds wherein combinations of $R_1$, $R_2$, $R_3$, $R_4$, substituents and $R_1'$, $R_2'$, $R_3'$, $R_4'$, substituents are bearing methylene chains $(CH_2)_n$, wherein n values may be within a range of from 2 to 15, especially of from 4 to 15, and alkyl groups of $C_2$-$C_{15}$, especially $C_4$-$C_{15}$, optionally including unsaturated bonds, such as C=C. The lowest Tg and reprocessing temperature of vitrimers are obtained, and the melt viscosities of such monomers are the lowest (compared to non-substituted ones or slightly substituted compounds, as mentioned above). For example, a Tg range values may be of from −50° C. to 150° C., the reprocessing temperatures being higher than the Tg range values.

In some alternate embodiments, the —S of the phenyl moiety in compound (A) may be in ortho or meta positions.

The invention also relates to a process for synthesizing a disulfide-containing benzoxazine monomer of formula (I) comprising the following steps consisting of:

a) providing a mixture comprising:
   an amino disulfide compound of formula (III): $H_2N$—R—$NH_2$ wherein R is as defined for the monomer of formula (I),
   an aldehyde derivative; and
   phenolic derivatives of formulae (IV) and (V)

(IV)

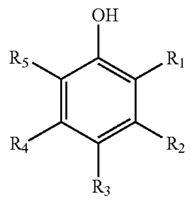

(V)

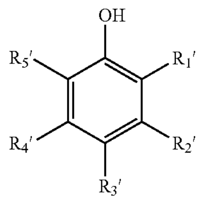

wherein combinations of $R_1$, $R_2$, $R_3$, $R_4$ and $R_1'$, $R_2'$, $R_3'$, $R_4'$ substituents are independently as defined above, and wherein $R_5$ and $R_5'$, independently, are H.

b) stirring the mixture under a temperature of from 50° C. to 130° C. for 1 h to 48 h, for obtaining the monomer of formula (I);

wherein the respective stoichiometry of the amino disulfide compound:aldehyde derivative:phenolic derivatives is $1{:}4{:}x_1{+}x_2$, with $x_1+x_2=2$ and $0<x_1;x_2<2$.

The disulfide-containing benzoxazine monomer of the invention is advantageously suited for obtaining polybenzoxazine derivatives vitrimers by a polymerization involving the benzoxazine ring opening and a self-polymerisation under heat.

As disclosed herein, it is shown that the specific starting reactants are providing a disulfide-containing benzoxazine monomer, which in turn, after polymerization, is giving the polybenzoxazine derivatives vitrimers comprising polymerized benzoxazine.

Accordingly, the benzoxazine ring, obtained from the reaction of the specific amino disulfide compound (formula (III)) and phenolic derivatives (formulae (IV) and (V)), which allows the material to be cross-linked (processed) upon heating, helps the reprocessing thanks to the reversible H-bonds it forms once cross-linked, and the dynamic disulfide bonds. Also, the benzoxazine ring moiety gives thermosetting properties such as high-temperature and flammability performance, high strength, thermal stability, low water absorption, chemical resistance, low melt viscosities, and near-zero shrinkage.

Disulfide bonds and hydrogen bonds are essential to form, in fine, polybenzoxazine derivatives vitrimers having dynamic network that allows the material to be recycled, reshaped and reprocessed.

Disulfide bonds are also essential to allow the adhesion of the vitrimer onto a substrate, especially on metallic substrates.

In various embodiments, the aldehyde derivative is selected from the group consisting of formaldehyde and paraformaldehyde, or mixture thereof.

For example, the process is performed with bio-based reactants, as one of the main components may be cardanol or derivatives thereof, eugenol and phloretic acid, or mixtures thereof.

The monomer synthesis may in various instances be solventless, even though a solvent could be added for the dissolution of starting reactants. The process involves a one-step synthesis, which is one of the advantages of the invention.

Advantageously, the synthesis may generally not require any further monomer purification for the invention to be implemented. However, the purification of the monomer, if needed, may be performed by any known technic (vacuum, distillation etc.)

The reaction mixture is stirred using a classical mechanical stirrer, or any non-limitative means.

The process requires a specific selection of the stoichiometry of the starting reactants. The stoichiometry of the phenolic derivative of formula (IV) is $x_1$, and that of the phenolic derivative of formula (V) is $x_2$, where $x_1+x_2=2$ and $0<x_1;x_2<2$.

The molar proportion of each phenolic derivative is not limited, one of the reasons is that $R_1$, $R_2$, $R_3$, $R_4$, $R_5$ and $R_1'$, $R_2'$, $R_3'$, $R_4'$, $R_5'$ respective combinations are, independently, identical.

Advantageously, the phenolic derivatives, independently, are at least one of those selected from the group consisting of phenol, guaiacol, creosol, vanillin, vanillic acid, eugenol, iso-eugenol, phloretic acid, coumaric acid, ferulic acid, dihydroferrulic acid, cresols (o-, m- and/or p-), phenols substituted by moieties including at least one of 2 to 15 carbon atoms, such as $C_2$, $C_3$, $C_4$, $C_5$, $C_6$, $C_7$, $C_8$, $C_9$, $C_{10}$, $C_{11}$, $C_{12}$, $C_{13}$, $C_{14}$ and/or $C_{15}$ (o-, m- and/or p-), cardanol derivatives, anacardic acid, cardol, 2-methylcardol, urushiol, o-allylphenol, m-allylphenol, p-allylphenol, 3-(furan-2-yl)phenol and 1-(4-hydroxyphenyl)-1H-pyrrole-2,5-dione, or mixture thereof.

The process may be implemented by any known means known to the one skilled in the art, using appropriate vessel.

The synthesis of the monomer is carried out under heat, the temperature of the mixture being of from 60° C. to 130° C., depending on the nature of the reactants, i.e the melting temperature of the reactant medium, and/or of the solvent too. It may be advantageous to select the temperature values below the boiling point of the reactants and/or of the solvent.

The reaction duration (step b)) is of from 1 h to 48 h, depending on the kinetic of the reaction and on the presence or not of the solvent. In various instances, the reaction duration may be of from 1 h to 24 h, for example of from 5 h to 24 h, in various instances of from 7 h to 20 h.

In some embodiments, where the synthesis of the disulfide-containing benzoxazine monomer is carried out without any solvent, the reaction temperature may be in the range of values of from 60° C. to 120° C., reaction duration may then in various instances be of from 1 h to 24 h, for example of from 7 h to 20 h.

In some embodiments, where the synthesis of the disulfide-containing benzoxazine monomer is carried out with a solvent, the reaction temperature may be in the range of values of from 70° C. to 130° C., reaction duration may then in various instances be of from 5 h to 24 h, for example of from 7 h to 20 h. Any appropriate solvent may be used for dissolution of the starting reactants. The appropriate solvent may be selected from the group consisting of THF, dioxane, chloroform and toluene, or mixture thereof. Once the reaction is achieved, the solvent may be in various instances evaporated by classical means, under vacuum, for example.

The invention also relates to a process for preparing polybenzoxazine derivative vitrimers comprising the step of polymerization of a benzoxazine monomer of the invention or as obtainable by the above mentioned process at temperatures within the range of from 100° C. to 250° C. for 1 h to 24 h, for obtaining polybenzoxazine derivatives vitrimers.

According to the process for preparing the vitrimers of the invention, the polymerization step, which is a curing step, allows the benzoxazine ring to open and to react on itself to form a 3D network in which inter- and intra-molecular hydrogen bonds between amino groups and phenolic hydroxyls are formed (H. D. Kim, H. Ishida, *Macromolecules,* 36(22) (2003) 8320-8329; B. Kiskan, *React. Funct. Polym,* 129 (2018) 76-88). The polymerization duration is depending on the curing temperature and/or on the nature of the benzoxazine monomer. The polymerization temperature is selected for a given monomer to be higher than the temperature needed to synthesize the monomer. Generally, the higher the polymerization temperature, the shorter the curing duration. For example, when the temperature of the polymerization is 250° C., the curing duration may be of at least 1 h, and for a polymerization temperature of 100° C., the curing duration may be of no more than 48 h. In various instances, the curing temperature may be of from 150° C. to 200° C., for example of from 170° C. to 190° C., the latter range providing curing duration of from 1 h to 3 h, in various instances of from 1 h to 2.5 h. The polymerization may be performed by any known heating means, such as laser beam and infrared beam.

Advantageously, the process may be a process for producing/preparing polybenzoxazine derivative vitrimers presenting at least one characteristic selected from the group consisting of self-healing, reshaping, reprocessability, recycling, reversible adhesive properties, thermoset and insolubility to solvents, or mixtures thereof.

The polymerization temperature may be advantageously defined as being the maximum of the exothermic peak measured by Differential Scanning calorimetry (DSC). Once cooled, the shape of the vitrimer material is kept.

When the obtained vitrimer is reheated, for example at a temperature of from 50° C. to 200° C., the disulfide bonds are breaking and reorganizing, allowing the vitrimer to be reshaped, recycled or reprocessed. The hydrogen bonds, on which the polybenzoxazine structure is relying, are an asset allowing the mechanical cohesion of the vitrimer.

The process may also include a post-polymerization step consisting of a heating step which may in various instances be carried out at higher temperature than that the polymerization heating step.

The invention is also directed to polybenzoxazine derivative vitrimers, that may be obtained by the above depicted process, presenting at least one of the following characteristics:

(i) Tg values of from 0° C. to 250° C.; and (ii) Relaxation temperature values, above the Tg values, of from 0° C. to 250° C.

Advantageously, the vitrimers may also exhibit at least one of the following characteristics selected from the group consisting of:

a relaxation time of from 0.1 s to 2 h, in various instances of from 1 s to 1 h, for example of from 1 s to 30 min, the relaxation time being defined as the time needed at a predetermined temperature for the vitrimer to relax of 50% after the appliance of a strain. The vitrimer may be deformed between 0.1% to 100% of its initial size;

the activation energy related to relaxation times may be of from 10 kJ/mol to 300 kJ/mol, in various instances of from 20 kJ/mol to 200 kJ/mol; and the processing temperature may be of from 50° C. to 200° C., in various instances of from 70° C. to 150° C.

The vitrimers according to the invention may also in various instances exhibit the characteristics of behaving as a thermoset and/or an insolubility in solvents, such as $CHCl_3$, $CH_2Cl_2$, DMF, THF, aromatic solvents, such as toluene and/or xylene. Swelling properties are observed as an extent of from 0 to 500% of the initial weight thereof.

It should be emphasized that the presence of long alkyl chains, methylene chains and/or substituents bearing cyclic hydrocarbons containing N or O in the benzoxazine ring moiety of the monomer used to synthesize the vitrimer, may advantageously enhance the reprocessability of the benzoxazine derivatives vitrimers, in terms of processing temperature and viscosity in the molten state, as indicated above.

The vitrimers of the invention present self-healing, reshaping, reprocessability, recycling and reversible adhesive properties.

The vitrimers may constitute a layer on a substrate, better an intermediate layer between at least two substrates, such as metal, polymer, glass and ceramic material. The resulting composite material may be prepared by setting at least one disulfide-containing benzoxazine monomer on a substrate, better between two considered substrates then curing at a temperature providing the vitrimer without altering the integrity of the substrate(s). Each substrate may be different from the other.

Metallic substrates are not limited, and may be of aluminium, iron, steel and the like.

Polymer substrates may be of polycarbonate, acrylic, polyamide, polyethylene or terephthalate.

Disulfide based benzoxazine vitrimers may then be advantageously used in non limited various fields of technologies, such electronics, aerospace, defense and automotive fields.

The invention also relates to a process for producing a material comprising at least one substrate coated with a polybenzoxazine derivative vitrimer of the invention presenting at least one characteristic selected from the group consisting of self-healing, reshaping, reprocessability, recycling, reversible adhesive properties, thermoset and insolubility to solvents, or mixtures thereof, the process comprising the steps of:

(i) depositing at least one disulfide-containing benzoxazine monomer of formula (I) onto the substrate;

(ii) polymerization of the benzoxazine monomer of step (i) on the substrate within the range of from 100° C. to 250° C. for 1 h to 24 h.

The invention also relates to a composition A comprising:

a) a benzoxazine derivative of formula (I), and b) at least one or more additional compounds of organic molecules types containing or not benzoxazine moieties.

In various instances, the organic molecules types may be polymers containing or not benzoxazine moieties.

The additional compound may be used to enhance the properties of either the monomer or the vitrimer (i.e., viscosity, mechanical and thermal properties), or both.

Polymers may be epoxy resins, bismaleimide resins, phenolic resins or benzoxazine resins, polyurethanes, polyamides, polyolefins, polyesters, rubbers. The benzoxazine derivative of formula (I) may be used in a weight ratio from 0.1 to 80% of the final composition.

The compound of formula (I) may be used to provide vitrimer properties to the above mentioned polymers (self-healing, reprocessing, etc. . . . ).

The invention also relates to a composition B comprising:

a) a benzoxazine derivative of formula (I), and b) a material selected from the group consisting of fillers, fibers, pigments, dyes, and plasticizer.

The additional compound may be used to enhance the properties of either the monomer or the vitrimer (i.e., viscosity, mechanical and thermal properties), or both.

The additional compound could be carbon fibers, glass fibers, clays, carbon black, silica, carbon nanotubes, graphene, any known means for the thermal or the mechanical reinforcement of composites.

The invention also concerns a use of the vitrimer according to the invention as a reversible adhesive, sealant, coating or encapsulating systems for substrates selected from the group consisting of a metal, polymer, glass and ceramic material. In various instances, the metal and the polymer are as above defined.

The invention also relates to a use of the vitrimer according to the invention in 3D printing processes or in additive manufacturing processes.

DRAWINGS

Other features and advantages of the present invention will be readily understood from the following detailed description and drawings among them:

Figure 5:
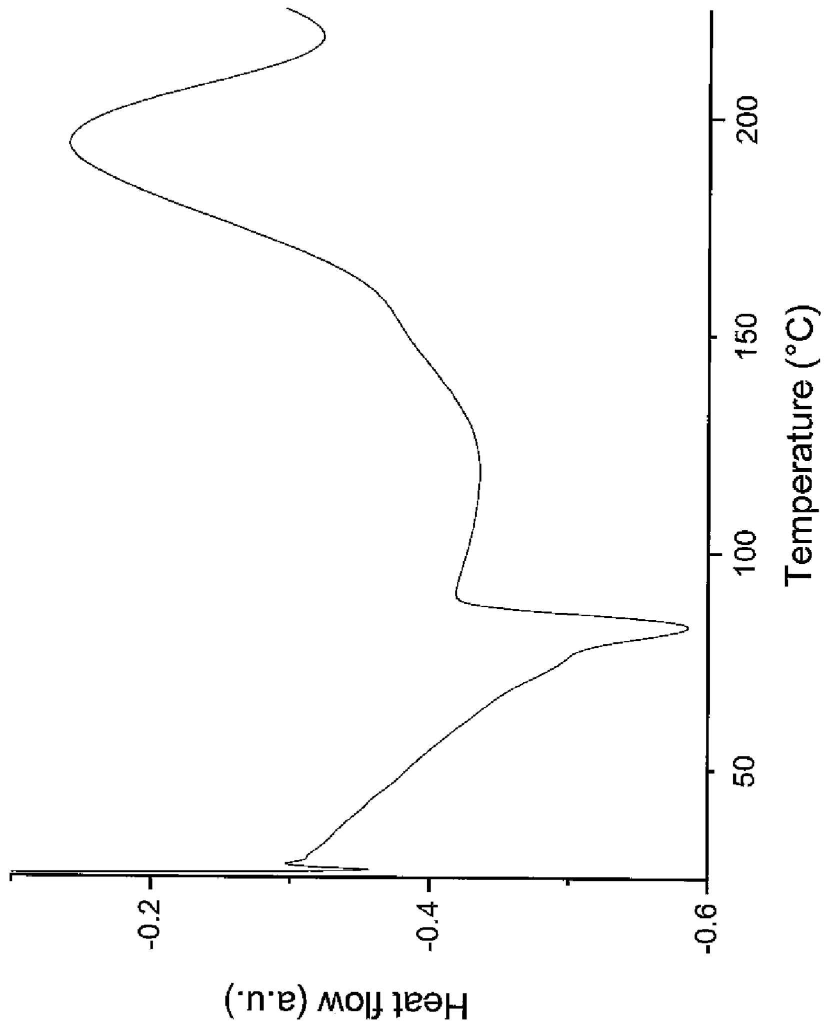

FIG. 5 displays the DSC curve of cardanol benzoxazine monomer[[;]], in accordance with various embodiments of the present invention.

Figure 6:
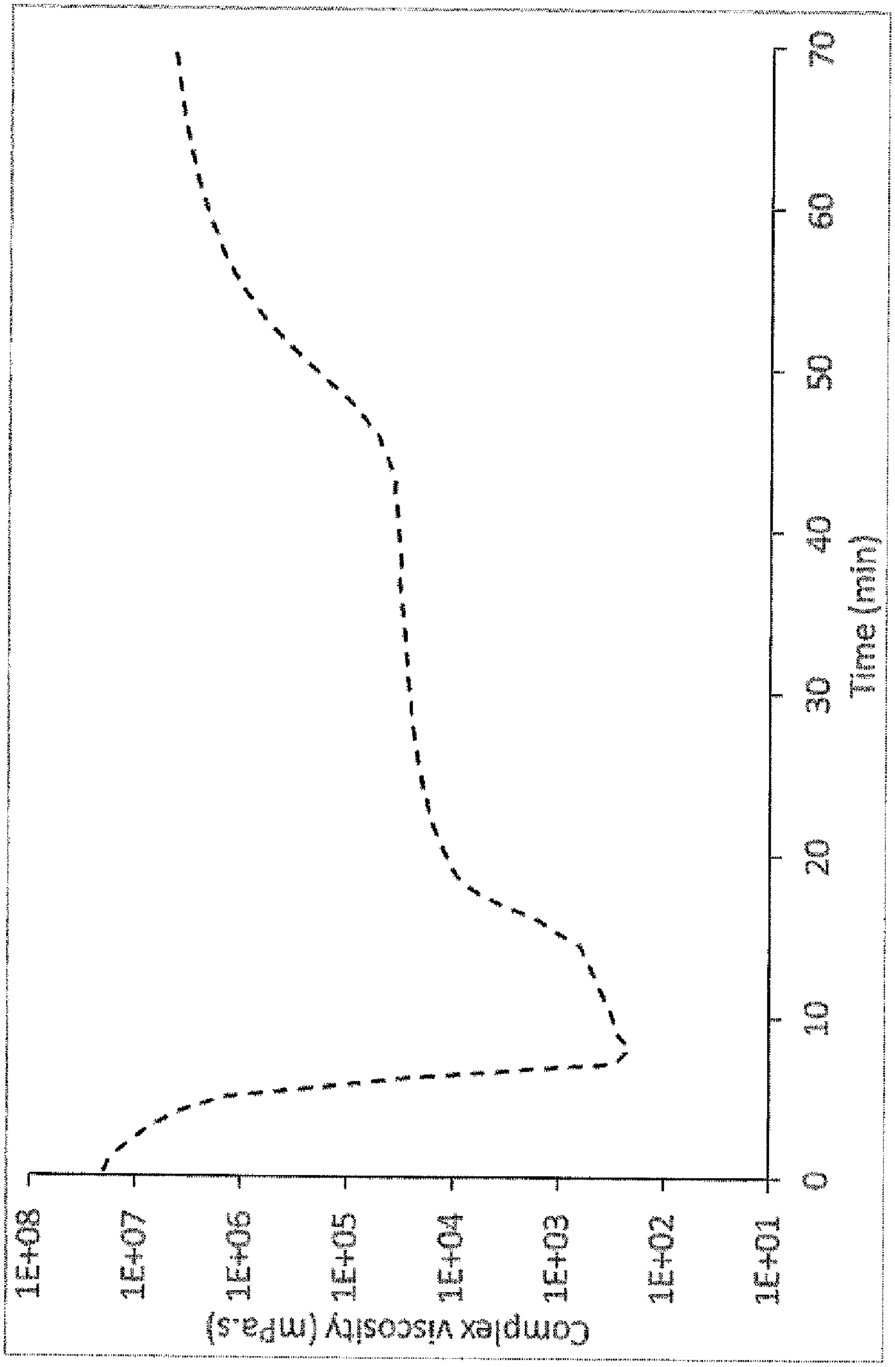

FIG. 6 displays a rheogram of the cardanol derivatives benzoxazine monomer—Evolution of the complex viscosity upon heating at 170° C.; in accordance with various embodiments of the present invention.

Figure 7:
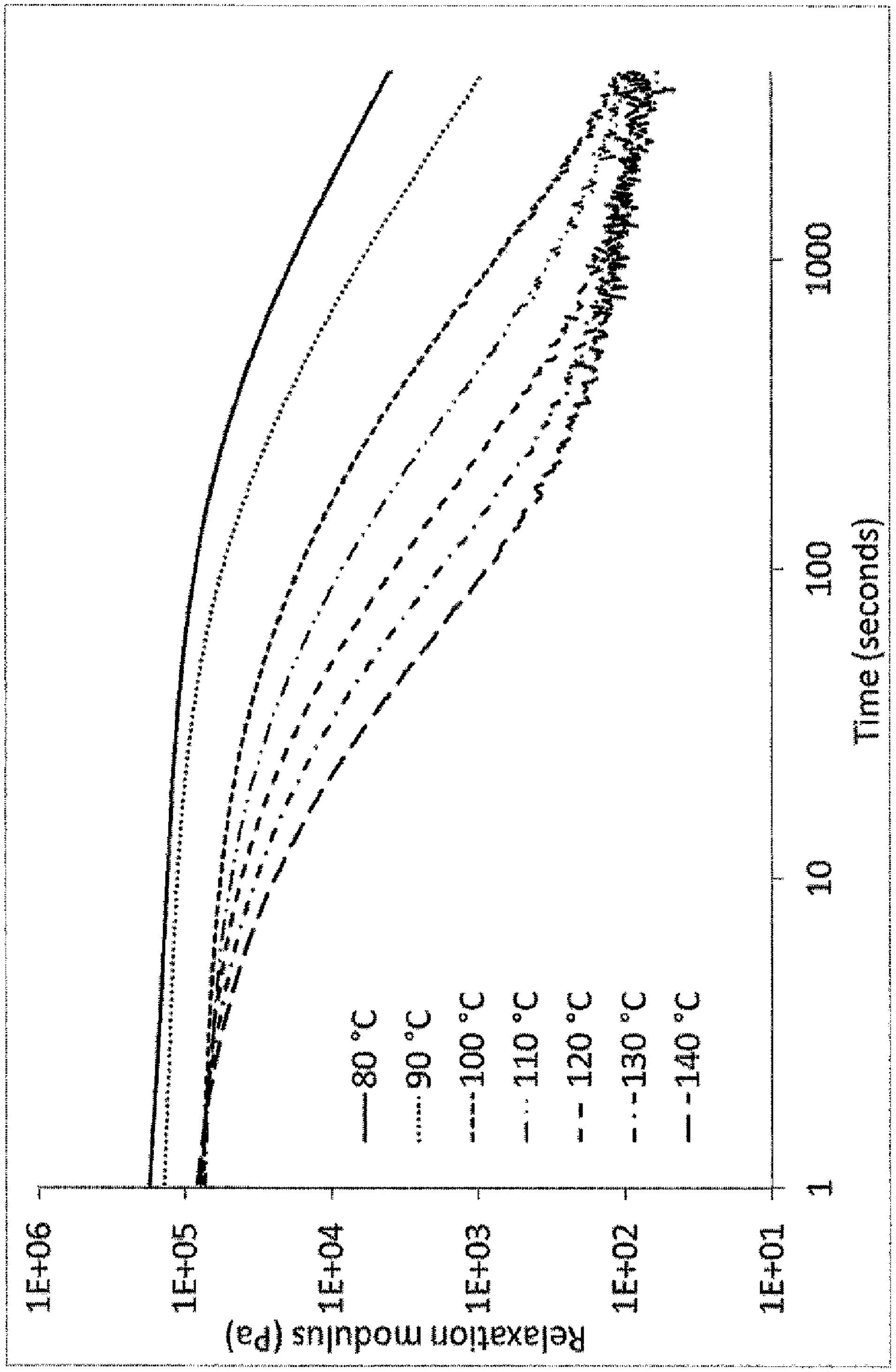

FIG. 7 shows the evolution of the relaxation modulus of a vitrimer obtained through the curing of the cardanol benzoxazine monomer, in accordance with various embodiments of the present invention.

Figure 8:
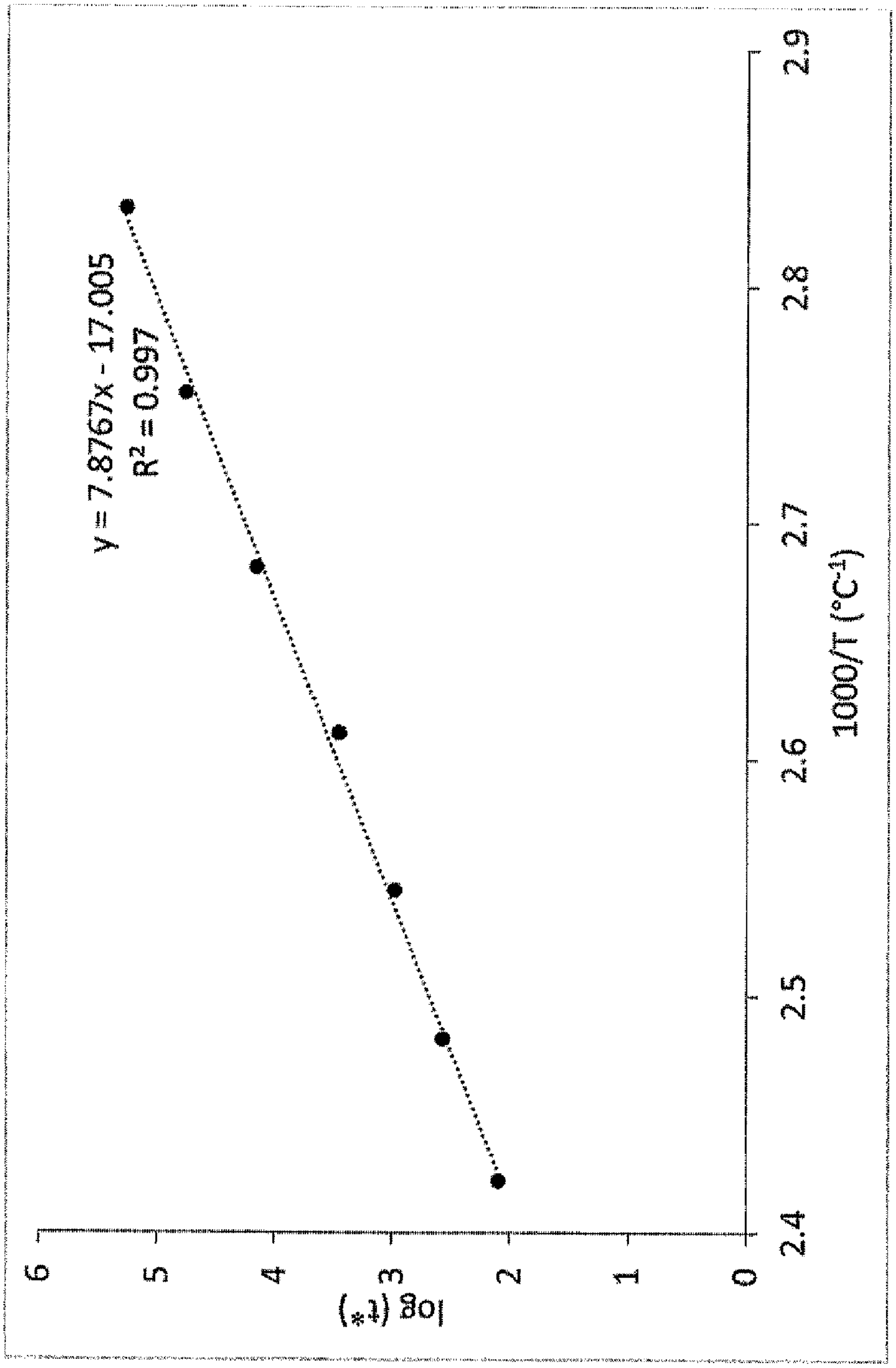

FIG. 8 show the evolution of the relaxation time t* as a function of 1000/T, in accordance with various embodiments of the present invention.

Figure 9:
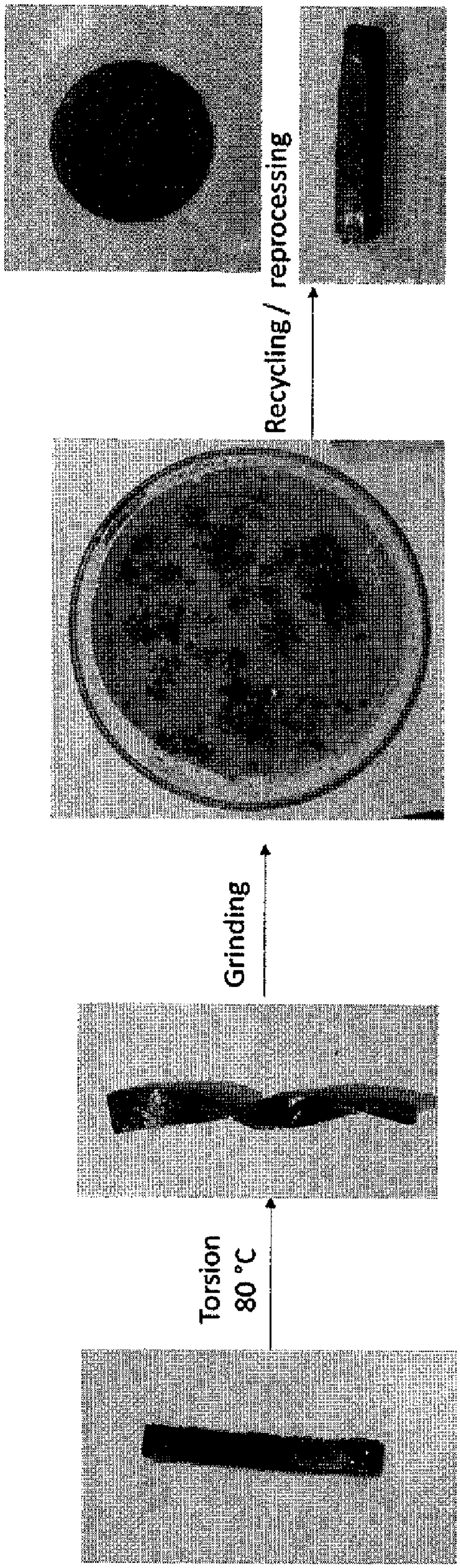

FIG. 9 is a schematic view of the ability of recycling/reprocessing of a vitrimer obtained through the curing of the cardanol benzoxazine monomer, in accordance with various embodiments of the present invention.

Figure 10:
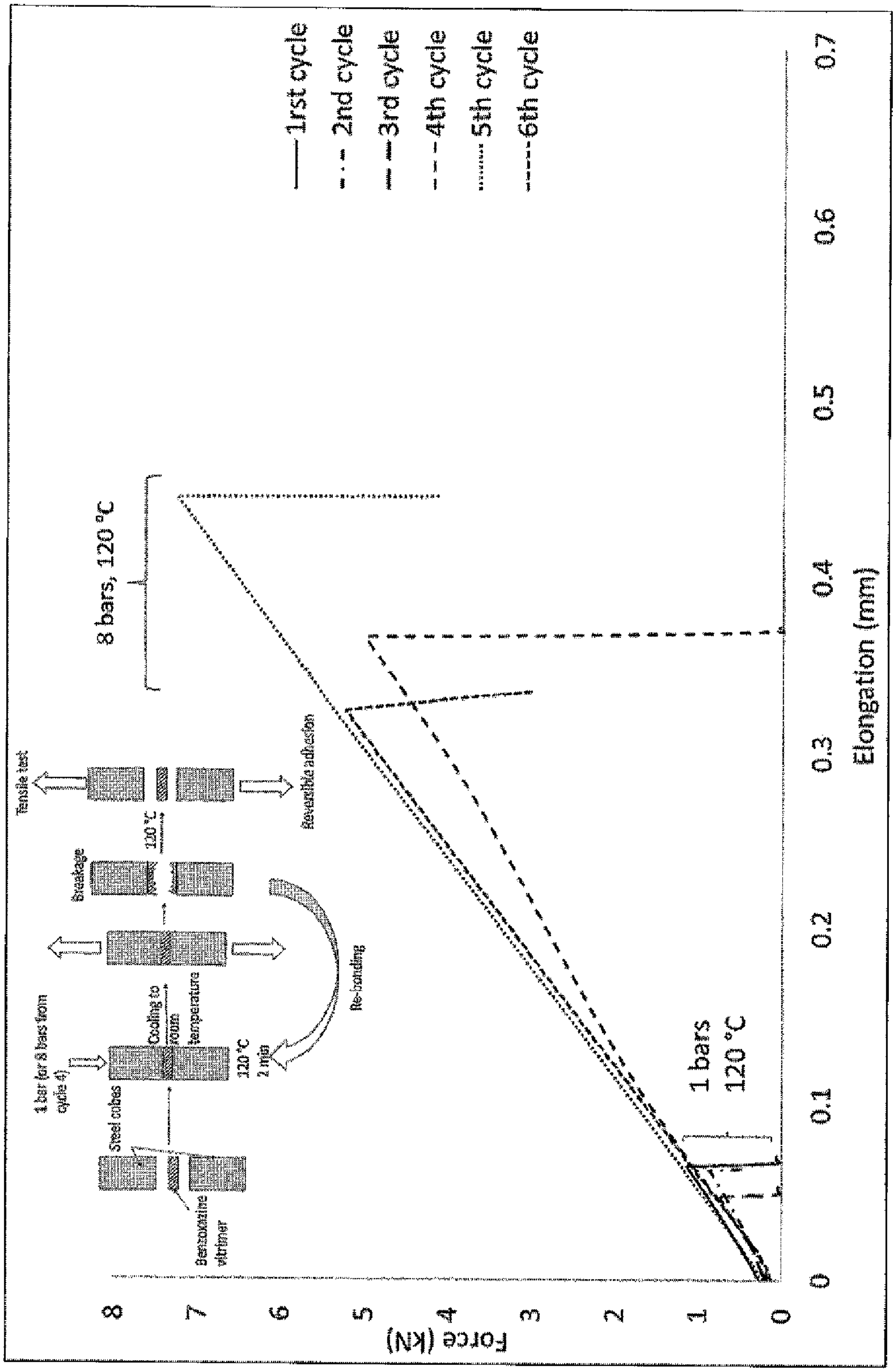

FIG. 10 shows the evolution of the adhesive strength of a vitrimer of the Example 2 used to glue two steel blocks as a function of the number of breakage cycles, in accordance with various embodiments of the present invention.

Figure 11:
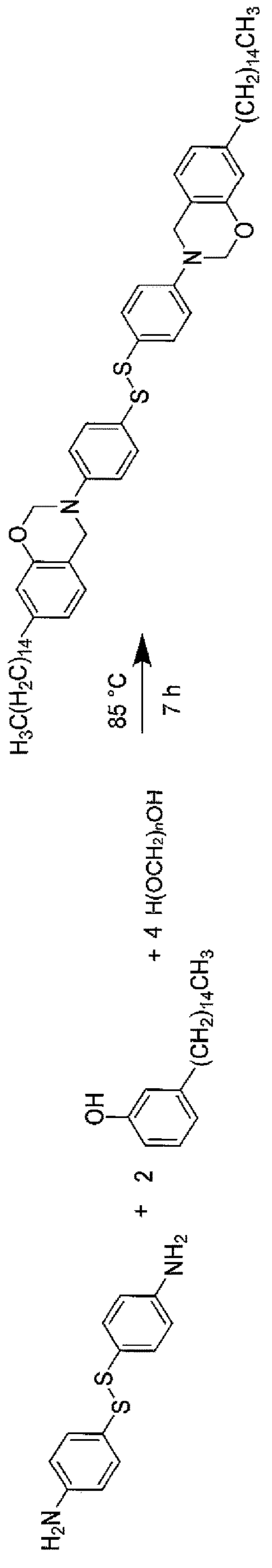

FIG. 11 shows a synthesis of a benzoxazine monomer from 3-pentadecylphenol as a phenolic derivative, in accordance with various embodiments of the present invention.

Figure 12:
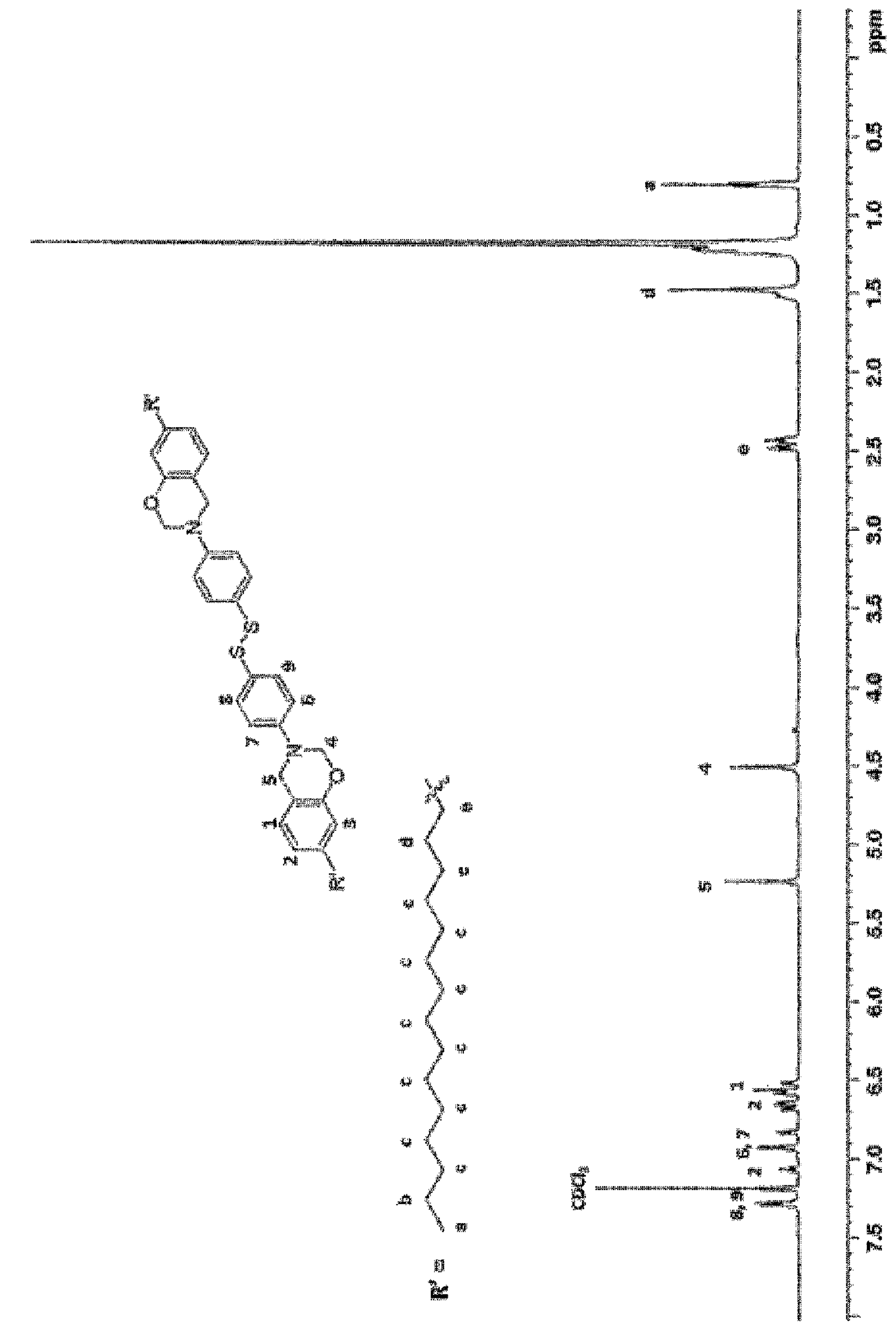

FIG. 12 shows a NMR spectrum of 3-pentadecylphenol benzoxazine monomer, in accordance with various embodiments of the present invention.

Figure 13:
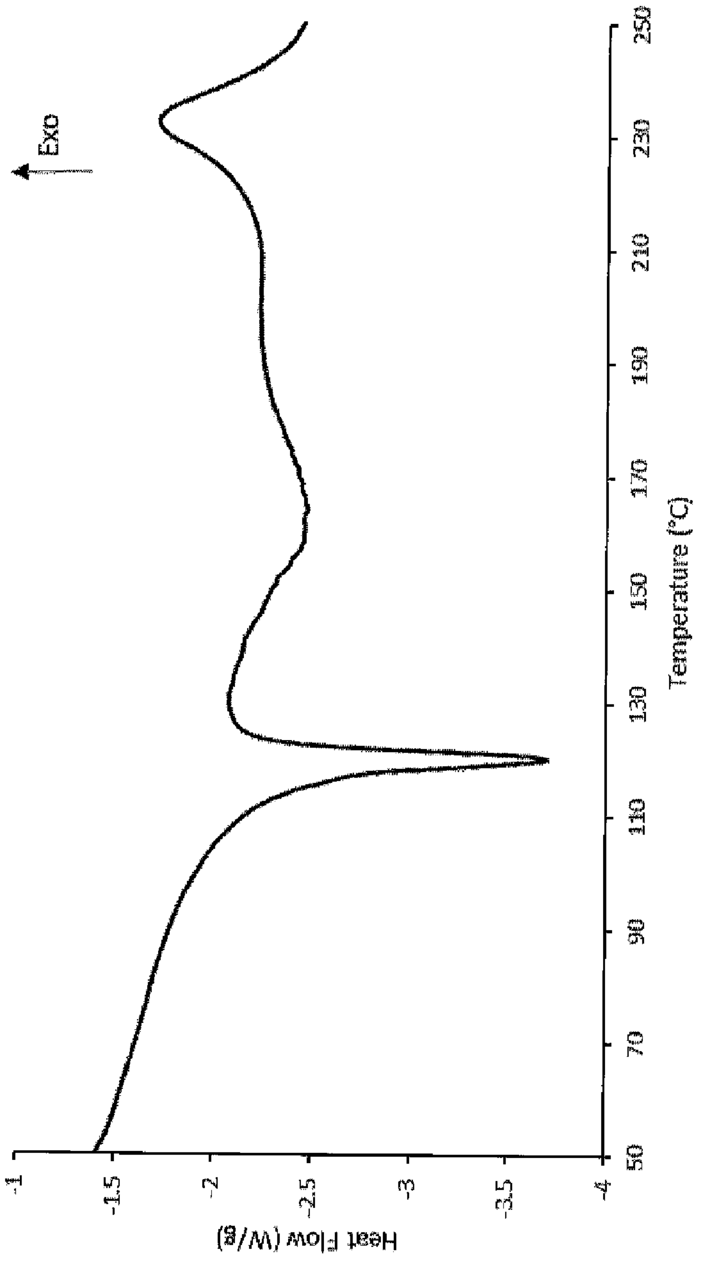

FIG. 13 displays the DSC curve of 3-pentadecylphenol benzoxazine monomer, in accordance with various embodiments of the present invention.

Figure 14:
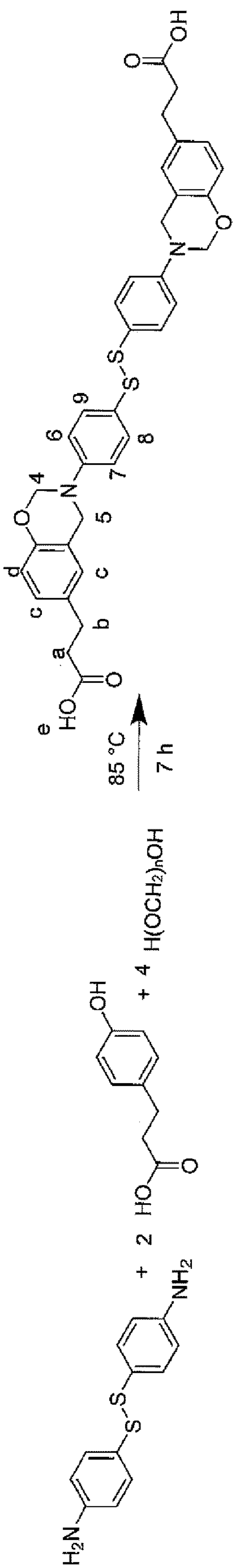

FIG. 14 shows a synthesis of a benzoxazine monomer from phloretic acid as a phenolic derivative, in accordance with various embodiments of the present invention.

Figure 15:
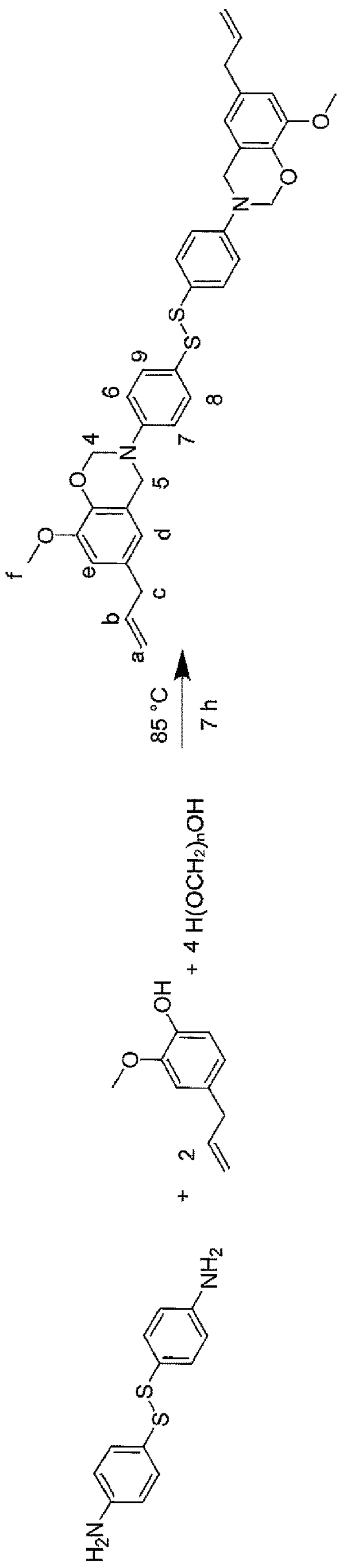

FIG. 15 shows a synthesis of a benzoxazine monomer from eugenol as a phenolic derivative, in accordance with various embodiments of the present invention.

DETAILED DESCRIPTION

Example 1: Synthesis of a Benzoxazine Monomer from Cardanol as a Phenolic Derivative Synthesis of disulfide-containing benzoxazine monomer was carried out with a mixture of cardanol (CAR) and 4-aminophenyl disulfide (4apds) and paraformaldehyde (PFA) reactants (FIG. 1).

Cardanol (5.97 g, 2 eq, 0.02 mol), 4-apds (2.48 g, 1 eq, 0.01 mol) and paraformaldehyde (1.20 g, 4 eq, 0.04 mol) were added at room temperature in a 100 ml round bottom flask. The flask was heated with an oil bath at 70° C. during 7 h and the reaction media was stirred with a mechanical stirrer. The reaction product was a yellow wax and was used without further purifications for the elaboration of vitrimer materials.

Figure 1:
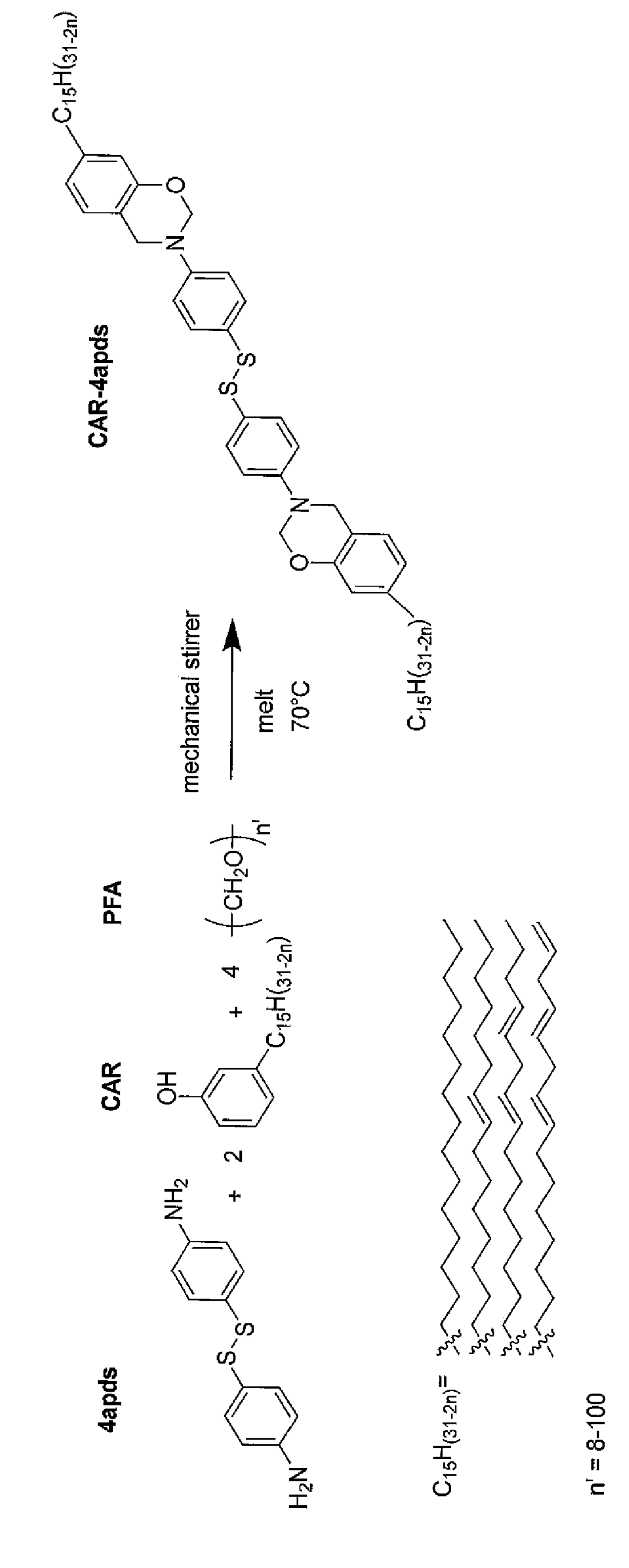
FIG. 1 shows a synthesis reaction of a benzoxazine monomer from cardanol as a phenolic derivative, in accordance with various embodiments of the present invention.
Figure 3:
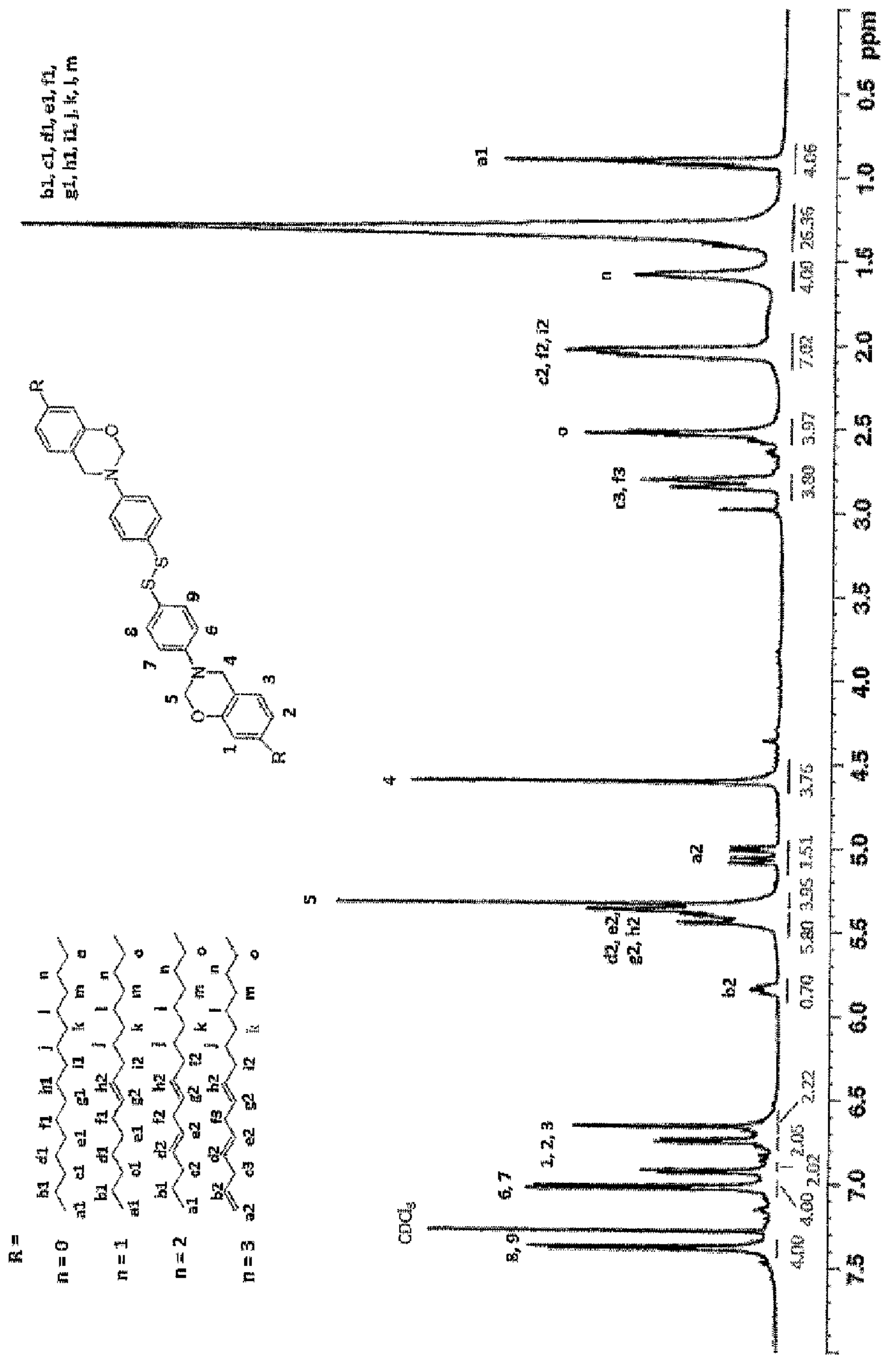
FIG. 3 is a NMR spectrum of the cardanol benzoxazine monomer, in accordance with various embodiments of the present invention.

The FIG. 3 is displaying the NMR spectrum (AVANCE III HD Bruker spectrometer) of cardanol derivatives benzoxazine monomer with various n values, as showed in FIG. 1.

Figure 4:
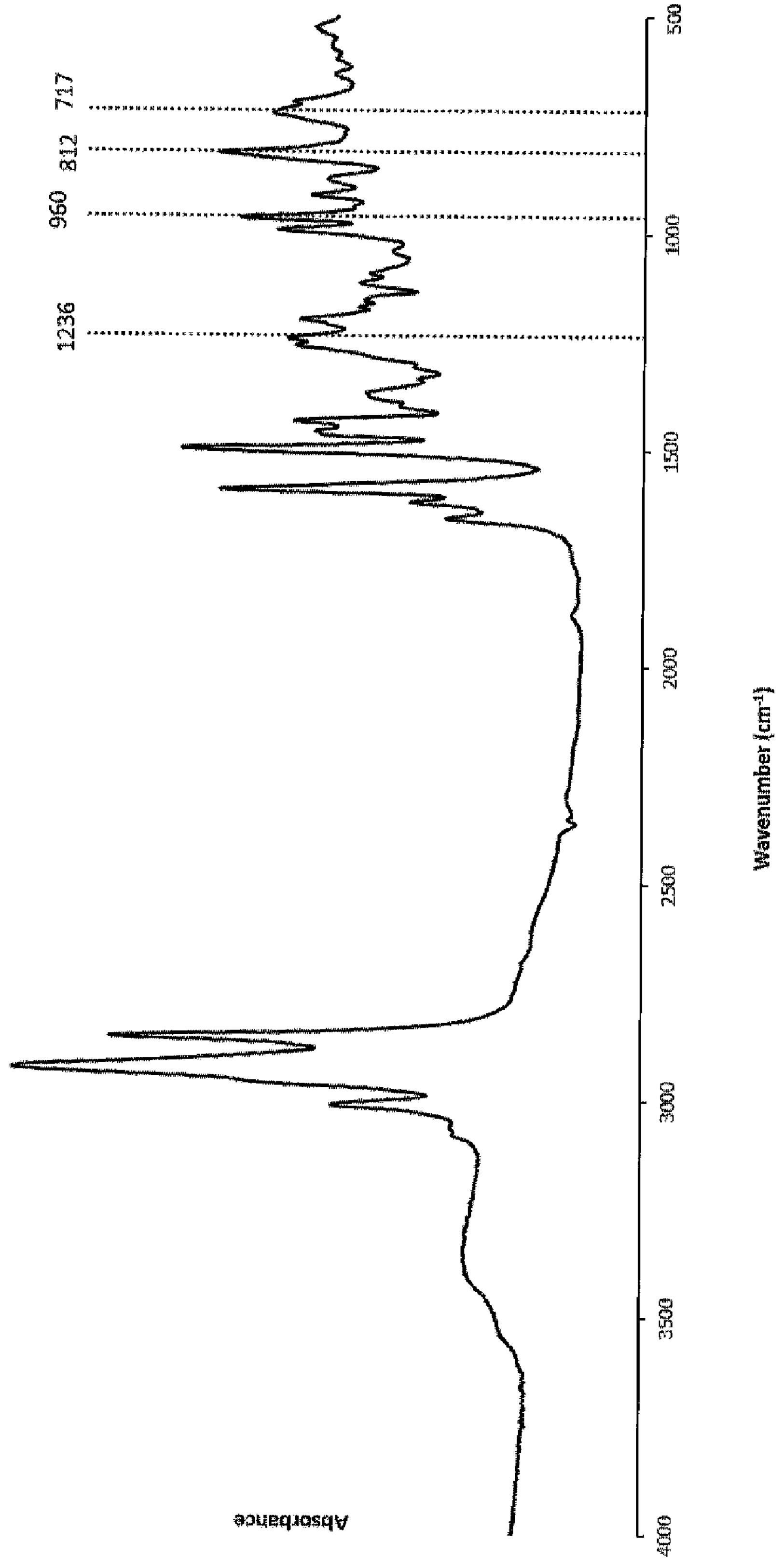
FIG. 4 is a FTIR spectrum of cardanol derivatives benzoxazine monomer, in accordance with various embodiments of the present invention.

FIG. 4 is showing an FTIR spectrum (Bruker TENSOR 27) of cardanol derivatives benzoxazine monomer with various n values.

The DSC results (FIG. 5) were obtained using an apparatus (Netzsch DSC 204 F1 Phoenix apparatus) with 10° C./min in an inert atmosphere. The DSC curve shows an exothermic peak starting at a temperature of 130° C., with a maximum located at 194° C., corresponding to the ring opening of the benzoxazine moiety upon heating.

The rheogram of the cardanol derivatives benzoxazine monomer is showed in FIG. 6.

The rheogram is performed under the following conditions: 1 Hz, with linear amplitude from 1 to 0.1%; 25 mm plates. The test is performed following a heating ramp from 100° C. to 170° C. at 10° C./min followed by an isothermal measurement at 170° C.

The test is showing the evolution of the complex viscosity as a function of time. The monomer is first softening as attested by the decrease of its complex viscosity, reaching a value of 100 mPa·s, meaning it can be easily processed by typical processing tool like infusion, etc.

After 15 minutes, the complex viscosity is increasing to $3.10^4$ mPa·s due to the benzoxazine ring opening and the first step of reaction. A second gelation is observed after 50 minutes as the crosslinking process is being achieved.

Figure 2:
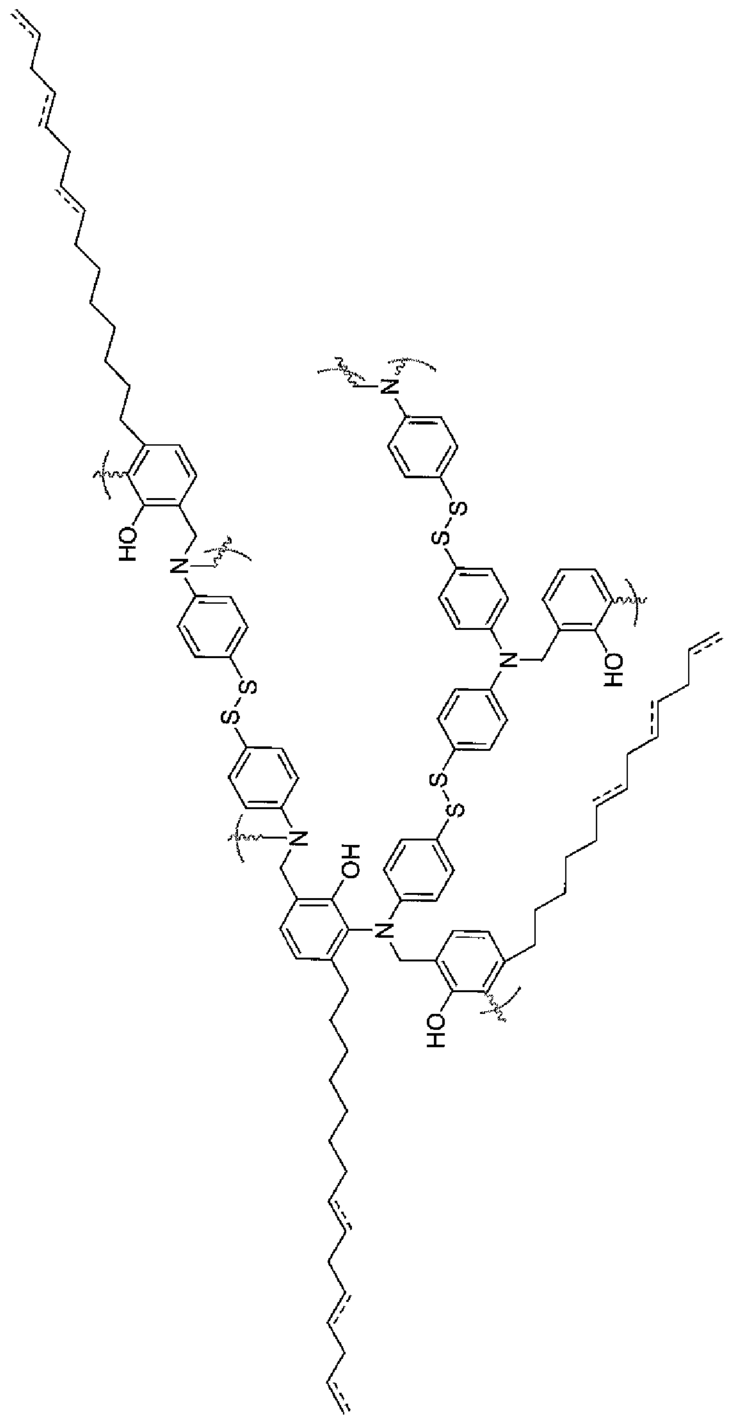
FIG. 2 shows a network for a vitrimer obtained through the curing of the cardanol benzoxazine monomer (schematized form), in accordance with various embodiments of the present invention.

Example 2: Synthesis of a Vitrimer Obtained Through the Curing of the Cardanol Derivatives Benzoxazine Monomer The benzoxazine monomer obtained in Example 1 was polymerized in a Teflon mold at 170° C. during 1 h, followed by a post cure of 30 minutes at 190° C., for the obtention of a cardanol derivatives polybenzoxazine vitrimer material (FIG. 2).

Pieces of the samples were immersed in DMF, toluene and water to measure their ability to swell. In toluene and DMF, the samples swell of 430% and 300%, respectively. In water, it does not swell.

The Tg of the material, defined as the maximum of the loss modulus measured by rheological measurement, is 50° C.

The FIG. 7 is showing the evolution of the relaxation modulus of the cardanol derivatives benzoxazine vitrimer at different temperatures as evidence of the vitrimer behavior. The drop of relaxation modulus is representative of the shape changes of the material. At 80° C., it takes 89 s for the material to lose 50% of its modulus. At 120° C., it takes 11 seconds. The relaxation temperature of the material is comprised between 50 and 150° C.

The evolution of relaxation time, defined as the time needed at a defined temperature for the material to relax of 50% of its initial modulus, is reported on FIG. 8, as a function of 1000/T. The evolution of ln(t*) as a function of 1000/T is linear, and is following an Arrhenius law, which is evidence of the associative behaviour of the vitrimer. The activation energy of the material can be calculated from the slope of the trendline, and is 65 kJ/mol.

The reprocessing temperature of the material is between 80° C. and 120° C.

FIG. 9 shows an example of the vitrimer of the Example 2 that has undergone a torsion at 80° C., then a grinding step and reshape and reprocess steps.

FIG. 10 shows the evolution of the adhesive strength of the vitrimer of the Example 2 used to glue two steel blocks. A scheme is reported onto the figure for the sake of clarity of the test. After each tensile test leading to the break of the assembly, the two blocks were re-assembled together by heating them and the vitrimer of the Example 2 at 120° C. for 10 minutes under a pressure of 1 bar. Initially the adhesion strength was measured to be equal to 1.08 MPa, without showing any significant decrease after 3 break/healing steps. After that the third breakage, the assembly was rebonded by heating at 120° C. for 2 minutes and pressing at under 8 bars, leading to a clear increase of the adhesion strength (5 kN). After the breakage the assembly was reformed and retested 3 times, showing the rebonding ability. At the end of the 6th cycle, it was possible to disassembly the vitrimer from the cube by heating at 120° C. for 5 minutes and by pulling the steel cubes. After its cooling, it was possible to still use the vitrimer to bond the metal cubes.

Example 3: Synthesis of a Benzoxazine Monomer from 3-Pentadecylphenol as a Phenolic Derivative Synthesis of disulfide-containing benzoxazine monomer was carried out with a mixture of 3-pentadecylphenol (3-PDP) and 4-aminophenyl disulfide (4apds) and paraformaldehyde (PFA) reactants (FIG. 11).

3-pentadecylphenol (6.09 g, 2 eq, 0.02 mol), 4-apds (2.48 g, 1 eq, 0.01 mol) and paraformaldehyde (1.20 g, 4 eq, 0.04 mol) were added at room temperature in a 100 ml round bottom flask. The flask was heated with an oil bath at 85° C. during 7 h and the reaction media was stirred with a mechanical stirrer. The reaction product was a light yellow wax and was used without further purifications for the elaboration of vitrimer materials.

The FIG. 12 is displaying the NMR spectrum (AVANCE III HD Bruker spectrometer) of 3-pentadecylphenol derivatives benzoxazine monomer.

The DSC results (FIG. 13) were obtained using an apparatus (Netzsch DSC 204 F1 Phoenix apparatus) with 10° C./min in an inert atmosphere. The DSC curve shows a broad exothermic peak starting at a temperature of 170° C., with a maximum located at 232° C., corresponding to the ring opening of the benzoxazine moiety upon heating.

The curing of the 3-pentadecylphenol derivatives benzoxazine monomer was monitored by rheological measurement.

The rheogram is performed under the following conditions: 1 Hz, with linear amplitude from 1 to 0.1%; 25 mm plates. The test is performed following a heating ramp from 100° C. to 200° C. at 10° C./min followed by an isothermal measurement at 200° C.

The complex viscosity is recorded as a function of time. The monomer is first softening as attested by the decrease of its complex viscosity, reaching a value of 100 mPa·s, meaning it can be easily processed by typical processing tool like infusion, etc.

After 200 minutes, the complex viscosity is increasing to $10^4$ mPa·s due to the benzoxazine ring opening.

Example 4: Synthesis of a Vitrimer Obtained Through the Curing of the 3-Pentadecylphenol Benzoxazine Monomer The benzoxazine monomer obtained in Example 3 was polymerized in a Teflon mold at 200° C. during 2 h, followed by a post cure of 2 h minutes at 220° C., for the obtention of a 3-pentadecylphenol polybenzoxazine vitrimer material.

Pieces of the samples were immersed in DMF, toluene and water to measure their ability to swell. In toluene and DMF, the samples swell of 800% and 600%, respectively. In water, it does not swell.

The Tg of the material, defined as the maximum of the loss modulus measured by rheological measurement, is 18° C.

The evolution of the relaxation modulus of the 3-pentadecylphenol benzoxazine vitrimer was followed by rheology at different temperatures as an evidence of the vitrimer behavior. The drop of relaxation modulus is representative of the shape changes of the material. At 80° C., it takes 42 s for the material to lose 50% of its modulus. At 120° C., it takes 6 seconds. The relaxation temperature of the material is comprised between 40° C. and 150° C.

The reprocessing temperature of the material is between 40° C. and 120° C.

Example 5: Synthesis of a Benzoxazine Monomer from Phloretic Acid as a Phenolic Derivative Synthesis of disulfide-containing benzoxazine monomer was carried out with a mixture of phloretic acid (PA) and 4-aminophenyl disulfide (4apds) and paraformaldehyde (PFA) reactants (FIG. 14).

Phloretic acid (3.32 g, 2 eq, 0.02 mol), 4-apds (2.48 g, 1 eq, 0.01 mol) and paraformaldehyde (1.20 g, 4 eq, 0.04 mol) were added at room temperature in a 100 ml round bottom flask. The flask was heated with an oil bath at 85° C. during 7 h and the reaction media was stirred with a mechanical stirrer. The reaction product was a brown wax and was used without further purifications for the elaboration of vitrimer materials.

$^1$H NMR ($CDCl_3$): [a] 2.5-2.6 ppm; [b] 2.8-2.9 ppm; [4] 4.5 ppm; [5] 5.3 ppm; [1,2] 6.5-6.7 ppm; [d] 6.75 ppm; [6,7] 6.8-6.9 ppm; [3] 7.0 ppm; [c] 7.15 ppm; [8,9] 7.3 ppm; [e] 11.5 ppm.

The DSC results were obtained using an apparatus (Netzsch DSC 204 F1 Phoenix apparatus) with 10° C./min in an inert atmosphere. The DSC curve shows a broad exothermic peak starting at a temperature of 130° C., with a maximum located at 176° C., corresponding to the ring opening of the benzoxazine moiety upon heating.

The curing of the phloretic acid benzoxazine monomer was monitored by rheological measurement.

The rheogram is performed under the following conditions: 1 Hz, with linear amplitude from 1 to 0.1%; 25 mm plates. The test is performed following a heating ramp from 100° C. to 170° C. at 10° C./min followed by an isothermal measurement at 170° C.

The complex viscosity is recorded as a function of time. The monomer is first softening as attested by the decrease of its complex viscosity, reaching a value of 100 mPa·s, meaning it can be easily processed by typical processing tool like infusion, etc.

After 10 minutes, the complex viscosity is increasing to $4.10^4$ mPa·s due to the benzoxazine ring opening.

Example 6: Synthesis of a Vitrimer Obtained Through the Curing of the Phloretic Acid Benzoxazine Monomer The benzoxazine monomer obtained in Example 5 was polymerized in a Teflon mold at 170° C. during 2 h, followed by a post cure of 30 minutes at 190° C., for the obtention of a phloretic acid polybenzoxazine vitrimer material.

The evolution of the relaxation modulus of the phloretic acid benzoxazine vitrimer was followed by rheology at different temperatures as an evidence of the vitrimer behavior. The drop of relaxation modulus is representative of the shape changes of the material. At 150° C., it takes 95 minutes for the material to lose 50% of its modulus. The relaxation temperature of the material is comprised between 120 and 190° C.

The reprocessing temperature of the material is between 80° C. and 120° C.

Example 7: Synthesis of a Benzoxazine Monomer from Eugenol as a Phenolic Derivative Synthesis of disulfide-containing benzoxazine monomer was carried out with a mixture of eugenol (EUG) and 4-aminophenyl disulfide (4apds) and paraformaldehyde (PFA) reactants (FIG. 15).

Eugenol (3.28 g, 2 eq, 0.02 mol), 4-apds (2.48 g, 1 eq, 0.01 mol) and paraformaldehyde (1.20 g, 4 eq, 0.04 mol) were added at room temperature in a 100 ml round bottom flask. The flask was heated with an oil bath at 85° C. during 7 h and the reaction media was stirred with a mechanical stirrer. The reaction product was a brown wax and was used without further purifications for the elaboration of vitrimer materials.

$^1H$ NMR ($CDCl_3$): [c] 3.4 ppm; [f] 3.8-3.9; [4] 4.5 ppm; [a] 5.1-5.2 ppm; [5] 5.3 ppm; [b] 5.9 ppm; [d,e] 6.4-6.6 ppm; [1,2] 6.5-6.7 ppm; [6,7] 6.8-6.9 ppm; [3] 7.0 ppm; [8,9] 7.3 ppm.

The DSC results were obtained using an apparatus (Netzsch DSC 204 F1 Phoenix apparatus) with 10° C./min in an inert atmosphere. The DSC curve shows a broad exothermic peak starting at a temperature of 125° C., with a maximum located at 200° C., corresponding to the ring opening of the benzoxazine moiety upon heating.

The curing of the eugenol benzoxazine monomer was monitored by rheological measurement.

The rheogram is performed under the following conditions: 1 Hz, with linear amplitude from 1 to 0.1%; 25 mm plates. The test is performed following a heating ramp from 100° C. to 170° C. at 10° C./min followed by an isothermal measurement at 170° C.

The complex viscosity is recorded as a function of time. The monomer is first softening as attested by the decrease of its complex viscosity, reaching a value of 100 mPa·s, meaning it can be easily processed by typical processing tool like infusion, etc.

After 45 minutes, the complex viscosity is increasing to $2.10^4$ mPa·s due to the benzoxazine ring opening.

Example 8: Synthesis of a Vitrimer Obtained Through the Curing of the Eugenol Benzoxazine Monomer The benzoxazine monomer obtained in Example 7 was polymerized in a Teflon mold at 170° C. during 2 h, followed by a post cure of 30 minutes at 190° C., for the obtention of a eugenol derivatives polybenzoxazine vitrimer material.

The evolution of the relaxation modulus of the phloretic acid benzoxazine vitrimer was followed by rheology at different temperatures as an evidence of the vitrimer behavior. The drop of relaxation modulus is representative of the shape changes of the material. At 120° C., it takes 7 minutes for the material to lose 50% of its modulus. The relaxation temperature of the material is comprised between 50 and 150° C.

The reprocessing temperature of the material is between 120° C. and 180° C.

The invention claimed is:

1. A disulfide-containing benzoxazine monomer of formula I (I)

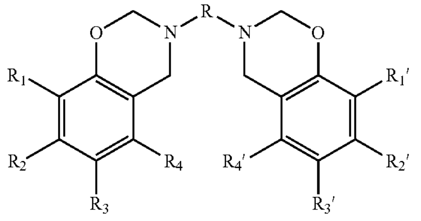

wherein R is:

(II)

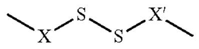

wherein, in formula (II), X and X' are, independently, at least one of:

one of a substituted and an unsubstituted aliphatic $C_1$-$C_{20}$ alkyl group;

at least one of a substituted and an unsubstituted aliphatic $C_2$-$C_{20}$ alkenyl group;

at least one of a substituted and an unsubstituted $C_6$-$C_{20}$ aryl group;

at least one of a substituted and an unsubstituted $C_6$-$C_{20}$ heteroaryl group;

at least one of a substituted and an unsubstituted $C_6$-$C_{20}$ heterocyclic group; and at least one of a substituted and an unsubstituted $C_3$-$C_8$ cycloalkyl group, and wherein a combination of $R_1$, $R_2$, $R_3$, $R_4$ substituents is selected from the group of the combinations consisting of $R_1$=$R_2$=$R_3$=$R_4$=H, $R_1$=$OCH_3$, $R_2$=$R_3$=$R_4$=H, $R_1$=$OCH_3$, $R_2$=$R_4$=H, $R_3$=alkyl group of $C_1$-$C_{15}$, $R_1$=$OCH_3$, $R_2$=$R_4$=H, $R_3$=CHO, $R_1$=$OCH_3$, $R_2$=$R_4$=H, $R_3$=$(CH_2)_{n:1\text{-}15}COOH$, $R_1$=$OCH_3$, $R_2$=$R_4$=H, $R_3$=$(CH_2)_{n:1\text{-}15}CH$=$CH_2$, $R_1$=$OCH_3$, $R_2$=$R_4$=H, $R_3$=CH=$CHCH_3$, $R_1$=$R_2$=$R_4$=H, $R_3$=$(CH_2)_{n:1\text{-}15}COOH$, $R_1$=$R_2$=$R_4$=H, $R_3$=CH=CHCOOH, $R_1$=$OCH_3$, $R_2$=$R_4$=H, $R_3$=CH=CHCOOH, at least one of $R_1$, $R_2$, $R_3$ and $R_4$ is an aliphatic alkyl group of $C_1$-$C_{15}$, the rest being H, $R_1$=$R_3$=$R_4$=H, and $R_2$ =

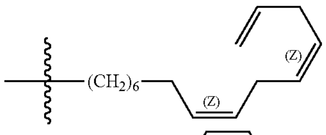

,

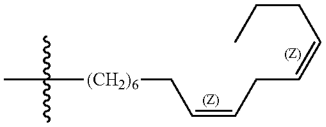

,

-continued
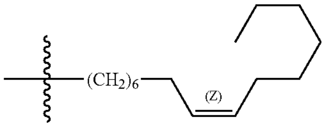
and/or
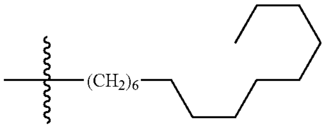
;
$R_3$═$R_4$═H, $R_1$═COOH
$R_2$ =
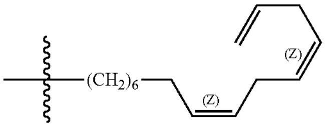
,
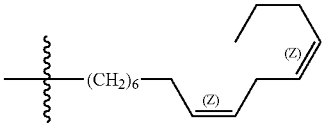
,
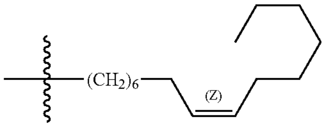
and/or
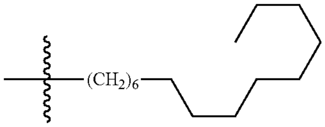
;
$R_1$═H, $R_2$═OH, $R_3$═H, and
$R_4$ =
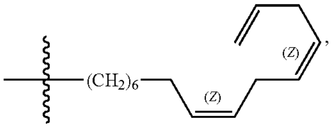
,
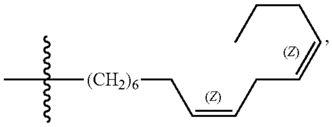
,
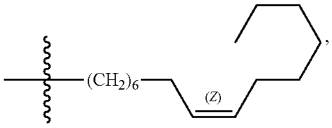
, and/or
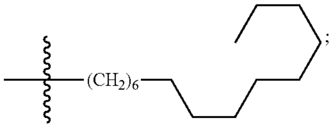
;
$R_1$═H, $R_3$═OH, $R_4$═H and
$R_2$ =
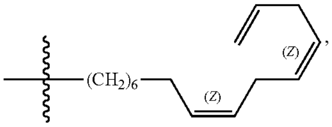
,
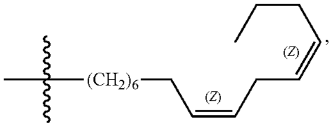
,
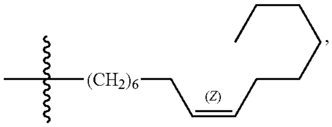
, and/or
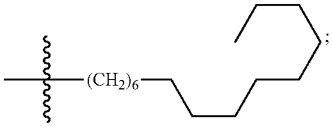
;
$R_1$═$CH_3$, $R_2$═OH, $R_3$═H,
$R_4$ =
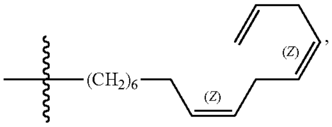
,
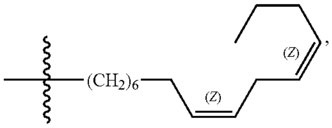
,
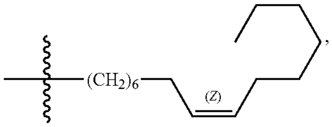
, and/or
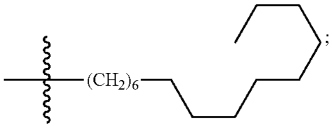
;
$R_3$═$R_4$═H, $R_1$═OH and
$R_2$ =
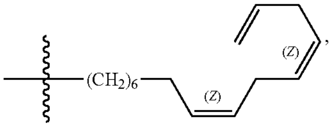
,
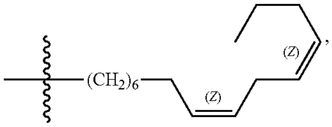
,
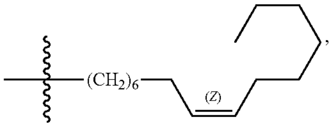
, and/or -continued

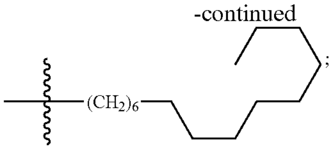

$R_2=R_3=R_4=H$ and $R_1=(CH_2)_{n:1-15}CH=CH_2$, $R_1=R_3=R_4=H$ and $R_2=(CH_2)_{n:1-15}CH=CH_2$, $R_1=R_2=R_4=H$ and $R_3=(CH_2)_{n:1-15}CH=CH_2$, $R_1=R_3=R_4=H$ and $R_2=$

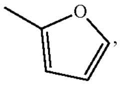

, and $R_1=R_2=R_4=H$ and $R_3=$

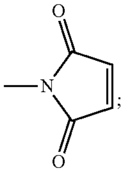

;

or mixture thereof wherein a combination of $R_1'$, $R_2'$, $R_3'$, $R_4'$, substituents is as defined for the combination of $R_1$, $R_2$, $R_3$, $R_4$, substituents and is independent thereof, the compound: N,N'-(disulfanediylbis(methylene))bis(6-(2H-benzo[e][1,3]oxazin-3 (4H)-yl)hexan-1-amine being excluded.

2. The disulfide-containing benzoxazine monomer of formula (I) according to claim 1, wherein, in formula (II), X and X' are, independently, at least one of:

one of a substituted and an unsubstituted aliphatic $C_1$-$C_{15}$ alkyl group;

at least one of a substituted and an unsubstituted aliphatic $C_2$-$C_{15}$ alkenyl group;

at least one of a substituted and an unsubstituted $C_6$-$C_{15}$ aryl group;

at least one of a substituted and an unsubstituted $C_6$-$C_{15}$ heteroaryl group;

at least one of a substituted and an unsubstituted $C_6$-$C_{15}$ heterocyclic group; and at least one of a substituted and an unsubstituted $C_3$-$C_6$ cycloalkyl group.

3. The disulfide-containing benzoxazine monomer of formula (I) according to claim 1, wherein R is selected from the group of moieties consisting of (A)

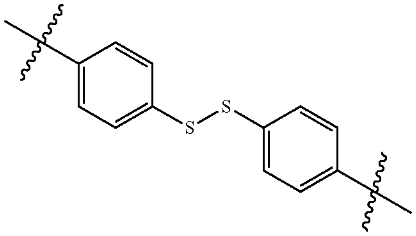

-continued

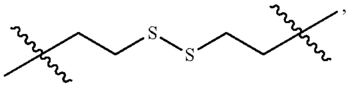

, and, independently, the combination of $R_1$, $R_2$, $R_3$, $R_4$ substituents and $R_1'$, $R_2'$, $R_3'$, $R_4'$, substituents being as defined for the combination of $R_1$, $R_2$, $R_3$, $R_4$ substituents and being independent thereof, is selected from the group of the combinations consisting of:

$R_1=OCH_3$, $R_2=R_4=H$, $R_3=$alkyl group of $C_1$-$C_{15}$, $R_1=OCH_3$, $R_2=R_4=H$, $R_5=(CH_2)_{n:1-15}COOH$, $R_1=OCH_3$, $R_2=R_4=H$, $R_3=(CH_2)_{n:1-15}CH=CH_2$, $R_1=R_2=R_4=H$, $R_3=(CH_2)_{n:1-15}COOH$, at least one of $R_1$, $R_2$, $R_3$ and $R_4$ is an aliphatic alkyl group of $C_1$-$C_{15}$, the rest being H, $R_1=R_3=R_4=H$, and at least one of:

$R_2=$

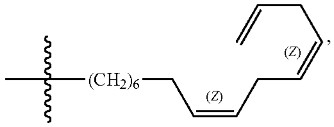

,

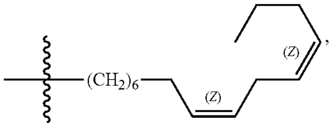

,

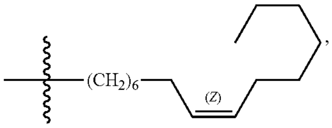

, and

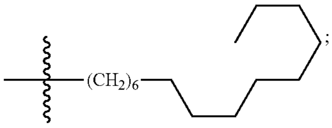

;

$R_3=R_4=H$, $R_1=COOH$ $R_2=$

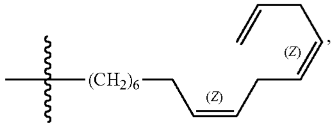

,

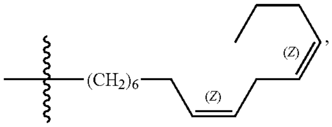

,

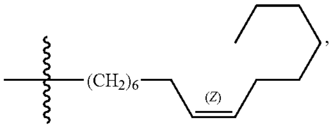

, and

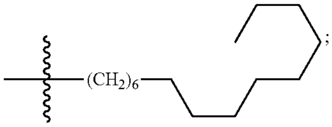

;

$R_1$=H, $R_2$=OH, $R_3$=H, and $R_4$ =

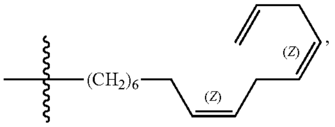

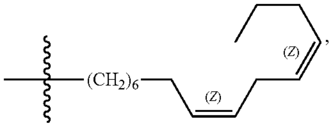

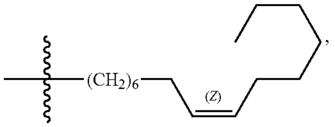

and

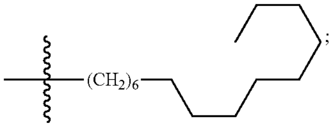

$R_1$=H, $R_3$=OH, $R_4$=H and $R_2$ =

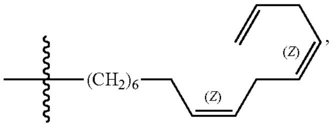

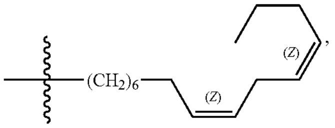

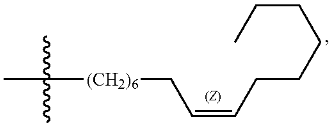

and

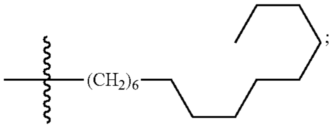

$R_1$=$CH_3$, $R_2$=OH, $R_3$=H, $R_4$ =

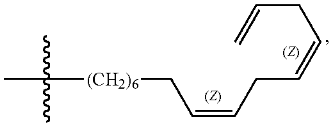

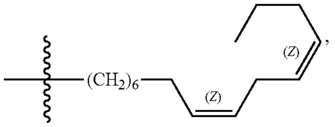

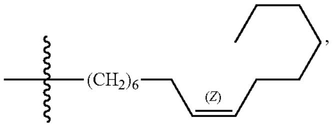

and

-continued

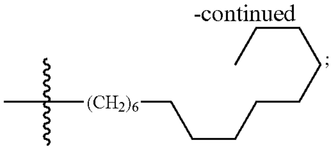

$R_3$=$R_4$=H, $R_1$=OH and $R_2$ =

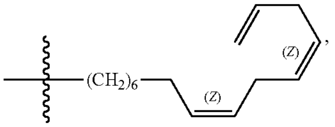

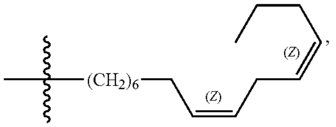

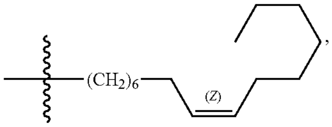

and

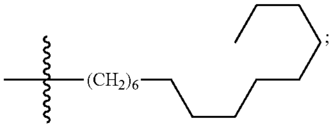

$R_2$=$R_3$=$R_4$=H and $R_1$=$(CH_2)_{n:1\text{-}15}CH$=$CH_2$, $R_1$=$R_3$=$R_4$=H and $R_2$=$(CH_2)_{n:1\text{-}15}CH$=$CH_2$, $R_1$=$R_2$=$R_4$=H and $R_3$=$(CH_2)_{n:1\text{-}15}CH$=$CH_2$, $R_1$=$R_3$=$R_4$=H and $R_2$=

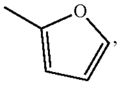

and $R_1$=$R_2$=$R_4$=H and $R_3$=

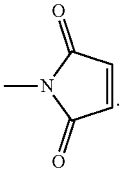

4. The disulfide-containing benzoxazine monomer according to claim 1, wherein the combinations of $R_1$, $R_2$, $R_3$, $R_4$ substituents and $R_1'$, $R_2'$, $R_3'$, $R_4'$ substituents are bearing methylene chains $(CH_2)_n$, wherein n values are within a range of from 2 to 15, and alkyl groups of $C_2$-$C_{15}$.

5. The disulfide-containing benzoxazine monomer of claim 1, formula (I), converted into a polybenzoxazine derivative vitrimer by a process comprising:

a) providing a mixture comprising:

an amino disulfide compound of formula (III): $H_2N$—R—$NH_2$ wherein R is as defined for the monomer of formula (I), an aldehyde derivative, selected from the group consisting of formaldehyde and paraformaldehyde, or mixtures thereof, and phenolic derivatives of formulae (IV) and (V)

(IV)

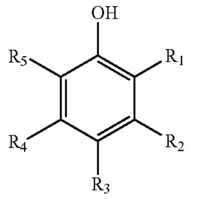

(V)

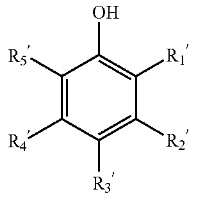

wherein combinations of $R_1$, $R_2$, $R_3$, $R_4$ and $R_1'$, $R_2'$, $R_3'$, $R_4'$ substituents are independently as defined in claim 1, and wherein $R_5$ and $R_5'$, independently, are H, b) stirring the mixture under a temperature of from 100° C. to 250° C. for 1 h to 24 h, for obtaining the polybenzoxazine derivative vitrimer of the monomer of formula (I);

wherein the respective stoichiometry of the amino disulfide compound:aldehyde derivative: phenolic derivatives is $1:4:x_1+x_2$, with $x_1+x_2=2$ and $0<x_1$; $x_2<2$;

the polybenzoxazine derivative vitrimer presenting at least one of the following characteristics:

(i) Tg values of from 0° C. to 250° C.; and (ii) Relaxation temperature values, above the Tg values, of from 0° C. to 250° C.

6. The disulfide-containing benzoxazine monomer according to claim 5, wherein the vitrimer exhibits at least one of the following characteristics selected from the group consisting of:

a relaxation time of from 0, 1 s to 2 h, the relaxation time being defined as the time needed at a predetermined temperature for the vitrimer to relax of 50% after the appliance of a strain;

the activation energy related to relaxation times of from 10 KJ/mol to 300 KJ/mol; and the reprocessing temperature of from 50° C. to 200° C.

7. The disulfide-containing benzoxazine monomer according to claim 6, wherein the vitrimer exhibits the characteristics of behaving at least one of as a thermoset and an insolubility in solvents, and swelling properties are as an extent of from 0 to 500% of the initial weight thereof.

8. The disulfide-containing benzoxazine monomer according to claim 6, wherein the vitrimer constitutes an intermediate layer between at least two substrates.

9. The disulfide-containing benzoxazine monomer according to claim 1, wherein, in formula (II), X and X' are, independently, at least one of:

one of a substituted and an unsubstituted aliphatic $C_1$-$C_{20}$ alkyl group containing heteroatoms;

at least one of a substituted and an unsubstituted aliphatic $C_2$-$C_{20}$ alkenyl group containing heteroatoms;

wherein the heteroatoms being selected from the groups consisting of N, O and S.

* * * * *